US011602329B2

(12) United States Patent
Miyazawa et al.

(10) Patent No.: US 11,602,329 B2
(45) Date of Patent: Mar. 14, 2023

(54) CONTROL DEVICE, CONTROL METHOD, CONTROL SYSTEM, AND NON-TRANSITORY RECORDING MEDIUM FOR SUPERIMPOSE DISPLAY

(71) Applicant: CANON KABUSHIKI KAISHA, Tokyo (JP)

(72) Inventors: Nobu Miyazawa, Yokohama (JP); Daiya Semba, Inagi (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 374 days.

(21) Appl. No.: 16/363,988

(22) Filed: Mar. 25, 2019

(65) Prior Publication Data
US 2019/0216436 A1  Jul. 18, 2019

Related U.S. Application Data

(63) Continuation of application No. PCT/JP2017/034989, filed on Sep. 27, 2017.

(30) Foreign Application Priority Data

Oct. 7, 2016  (JP) .............................. JP2016-198893

(51) Int. Cl.
*A61B 8/08* (2006.01)
*A61B 8/00* (2006.01)
*A61B 5/00* (2006.01)

(52) U.S. Cl.
CPC .......... *A61B 8/5207* (2013.01); *A61B 5/0095* (2013.01); *A61B 8/463* (2013.01);
(Continued)

(58) Field of Classification Search
CPC ..... A61B 8/5207; A61B 8/0095; A61B 8/463; A61B 8/465; A61B 8/467; A61B 8/5246;
(Continued)

(56) References Cited

U.S. PATENT DOCUMENTS 8,861,824 B2 * 10/2014 Nishimura ................ G06T 7/11
382/131
9,468,418 B2 * 10/2016 Higuchi .................... A61B 8/14
(Continued)

FOREIGN PATENT DOCUMENTS

JP          H0947438 A   *  2/1997
JP          11-169368 A      6/1999
(Continued)

OTHER PUBLICATIONS

A. Needles et al, "Developmentand Initial Application of a Fully Integrated Photoacoustic Micro-Ultrasound System", IEEE Transactions on Ultrasonics, Ferroelectrics, and Frequency Control, vol. 60, No. 5, pp. 888-897, May 2013 (Year: 2013).*
(Continued)

*Primary Examiner* — Joel Lamprecht
*Assistant Examiner* — Nyrobi Celestine
(74) *Attorney, Agent, or Firm* — Canon U.S.A., Inc. IP Division

(57) ABSTRACT

A control device acquires a plurality of images including an ultrasound image and a photoacoustic image taken in an examination, selects a first image and a second image to be displayed superimposed on the first image, based on information relating to the examination, and generates an object for outputting at least information for displaying the second image superimposed on the first image to an external device.

16 Claims, 19 Drawing Sheets

(52) U.S. Cl.
CPC .............. *A61B 8/465* (2013.01); *A61B 8/467* (2013.01); *A61B 8/5246* (2013.01); *A61B 8/5292* (2013.01); *A61B 8/54* (2013.01)

(58) Field of Classification Search
CPC ..... A61B 8/5292; A61B 8/54; A61B 5/02007; A61B 5/0095
See application file for complete search history.

(56) References Cited

U.S. PATENT DOCUMENTS

| | | | | |
|---|---|---|---|---|
| 2004/0047497 | A1* | 3/2004 | Daw | G06T 19/00 |
| | | | | 382/128 |
| 2006/0229513 | A1* | 10/2006 | Wakai | G06T 5/50 |
| | | | | 600/407 |
| 2007/0078325 | A1* | 4/2007 | Fuimaono | A61B 5/055 |
| | | | | 600/407 |
| 2009/0010519 | A1* | 1/2009 | Wakai | G16H 30/20 |
| | | | | 382/131 |
| 2009/0099452 | A1* | 4/2009 | Hashimoto | A61B 8/481 |
| | | | | 600/443 |
| 2009/0268864 | A1* | 10/2009 | Nishida | A61B 6/502 |
| | | | | 378/37 |
| 2010/0177941 | A1* | 7/2010 | Shiozawa | G06T 7/0012 |
| | | | | 382/128 |
| 2012/0108960 | A1* | 5/2012 | Halmann | A61B 8/467 |
| | | | | 600/437 |
| 2013/0289381 | A1* | 10/2013 | Oraevsky | A61B 5/14552 |
| | | | | 600/407 |
| 2013/0290826 | A1* | 10/2013 | Niwa | G06Q 10/10 |
| | | | | 715/230 |
| 2013/0307863 | A1* | 11/2013 | Waki | G06T 7/0012 |
| | | | | 345/589 |
| 2014/0187903 | A1* | 7/2014 | Oyama | A61B 5/6885 |
| | | | | 600/407 |
| 2014/0187936 | A1* | 7/2014 | Nakamura | G06T 5/50 |
| | | | | 600/437 |
| 2014/0194723 | A1* | 7/2014 | Herzog | A61B 8/0825 |
| | | | | 600/407 |
| 2015/0011872 | A1* | 1/2015 | Koh | A61B 8/5261 |
| | | | | 600/424 |
| 2015/0201135 | A1* | 7/2015 | Oh | A61B 5/0035 |
| | | | | 348/163 |
| 2015/0250446 | A1* | 9/2015 | Kanayama | A61B 8/468 |
| | | | | 600/438 |
| 2016/0015364 | A1* | 1/2016 | Kurita | A61B 6/468 |
| | | | | 600/422 |
| 2018/0211392 | A1* | 7/2018 | Kim | G16H 30/20 |

FOREIGN PATENT DOCUMENTS

| | | | | | |
|---|---|---|---|---|---|
| JP | | 2005-21380 | A | | 1/2005 |
| JP | | 5364238 | B2 | * | 12/2013 |
| JP | | 2014-128320 | A | | 7/2014 |
| JP | | 2016030110 | A | * | 3/2016 |
| WO | WO-2014084201 | A1 | * | 6/2014 | ............ A61B 8/4416 |
| WO | WO-2014181633 | A1 | * | 11/2014 | ............ A61B 8/5292 |
| WO | WO-20150250446 | A1 | * | 11/2014 | |

OTHER PUBLICATIONS

JP-5364238-B2 (Year: 2013).*
WO-2014084201-A1 (Year: 2014).*

* cited by examiner

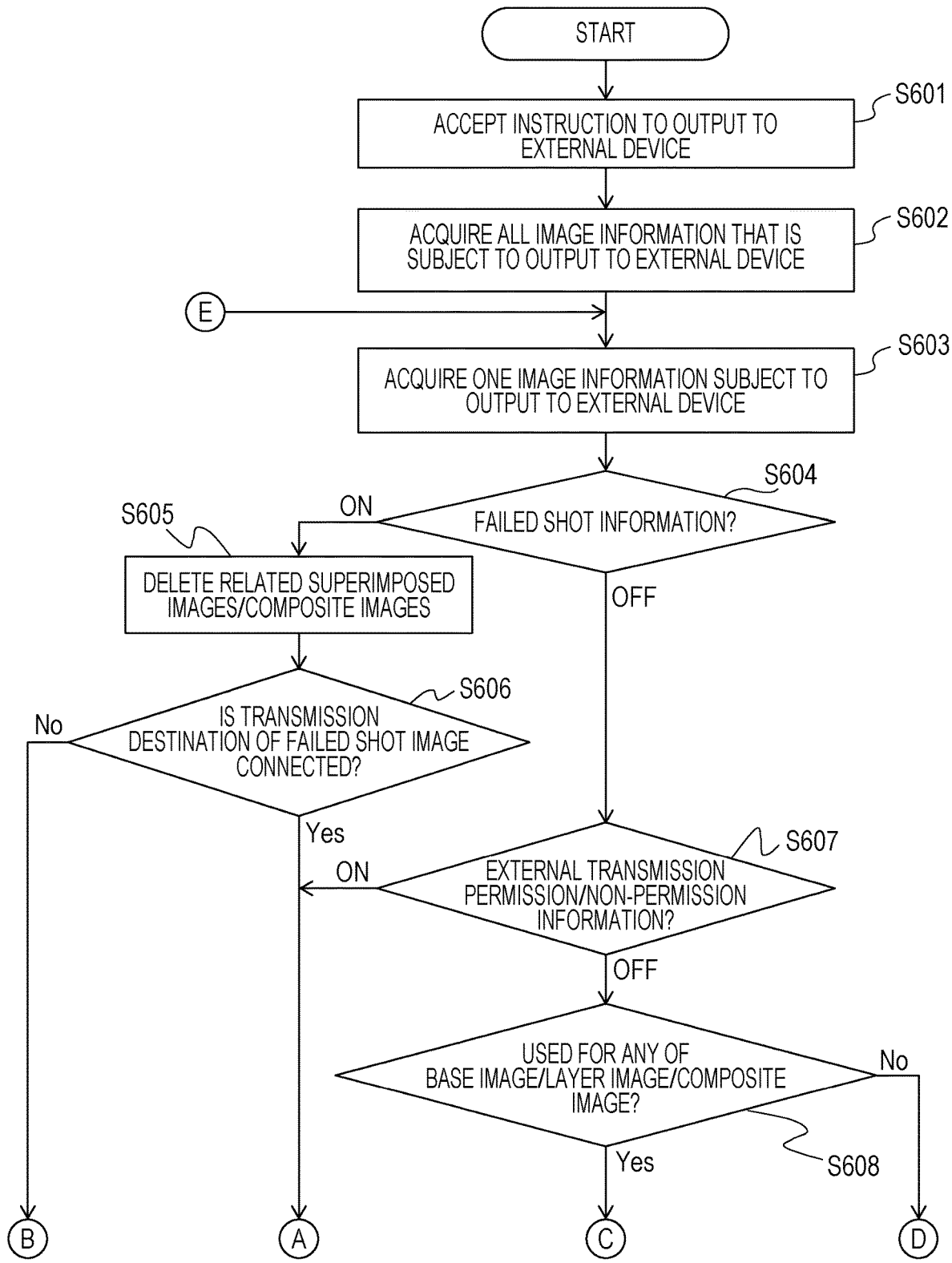

FIG. 9

| CONFIRMATION LIST OF EXTERNAL TRANSMISSION IMAGES | | | | | | |
|---|---|---|---|---|---|---|
| SHOOTING PROCEDURE NAME: ABDOMINAL EXAMINATION | | | | | | |
| BASE IMAGE | SUPERIMPOSED IMAGE 1 | SUPERIMPOSED IMAGE 2 | SUPERIMPOSED IMAGE 3 | SUPERIMPOSED IMAGE 4 | SUPERIMPOSED IMAGE 5 | |
| B-MODE IMAGE | | | | | | |
| CONTINUOUS WAVE DOPPLER | | | | | | |
| INITIAL ACOUSTIC PRESSURE [756 nm] | | | | | | |
| INITIAL ACOUSTIC PRESSURE [797 nm] | | | | | | |
| ABSORPTION COEFFICIENT [756 nm] | | | | | | |

FIG. 14A

SUPERIMPOSED IMAGE CUSTOMIZATION SETTINGS

SHOOTING PROCEDURE NAME: ABDOMINAL EXAMINATION ▼ | SUPERIMPOSED IMAGE | COMPOSITE IMAGE | ▲ | ADD | EDIT

| BASE IMAGE | SUPERIMPOSED IMAGE 1 | SUPERIMPOSED IMAGE 2 | SUPERIMPOSED IMAGE 3 | SUPERIMPOSED IMAGE 4 | SUPERIMPOSED IMAGE 5 |
|---|---|---|---|---|---|
| B-MODE IMAGE | LAYER IMAGE<br>・ABSORPTION COEFFICIENT<br>SUPERIMPOSING METHOD<br>・MASK | LAYER IMAGE<br>・COLOR DOPPLER<br>・Total-Hb<br>SUPERIMPOSING METHOD<br>・SUPERIMPOSING | | | |
| CONTINUOUS WAVE DOPPLER | | | | | |
| COLOR DOPPLER | | | | | |
| ABSORPTION COEFFICIENT | LAYER IMAGE<br>・Total-Hb<br>SUPERIMPOSING METHOD<br>・TRANSMISSIVE DISPLAY | | | | |
| Total-Hb | LAYER IMAGE<br>・Oxy-Hb<br>SUPERIMPOSING METHOD<br>・MIXED DISPLAY | LAYER IMAGE<br>・Deoxy-Hb<br>SUPERIMPOSING METHOD<br>・MIXED DISPLAY | | | |

CANCEL | OK

FIG. 14B

INDIVIDUAL SUPERIMPOSED IMAGE SETTINGS

SHOOTING PROCEDURE NAME: ABDOMINAL EXAMINATION

BASE IMAGE TYPE:
B-MODE ∨

SUPERIMPOSING/COMPOSITING IMAGE TYPE:

| ORDER OF SUPERIMPOSING | SUPERIMPOSING/ COMPOSITING | IMAGE TYPE |
|---|---|---|
| 1 | ON | ABSORPTION COEFFICIENT |
| 2 | OFF | OXYGEN SATURATION |
| 3 | OFF | Oxy-Hb |
| 4 | OFF | Deoxy-Hb |
| 5 | OFF | COLOR DOPPLER |
| 6 | OFF | INITIAL ACOUSTIC PRESSURE |
| 7 | OFF | FLUENCE |
| 8 | OFF | Total-Hb |
| 13 | OFF | M-MODE |

SUPERIMPOSING/COMPOSITING METHOD:
TRANSMISSIVE DISPLAY ∨    50 %

CANCEL — 1414
OK — 1415

1409
1410
1411
1412
1413

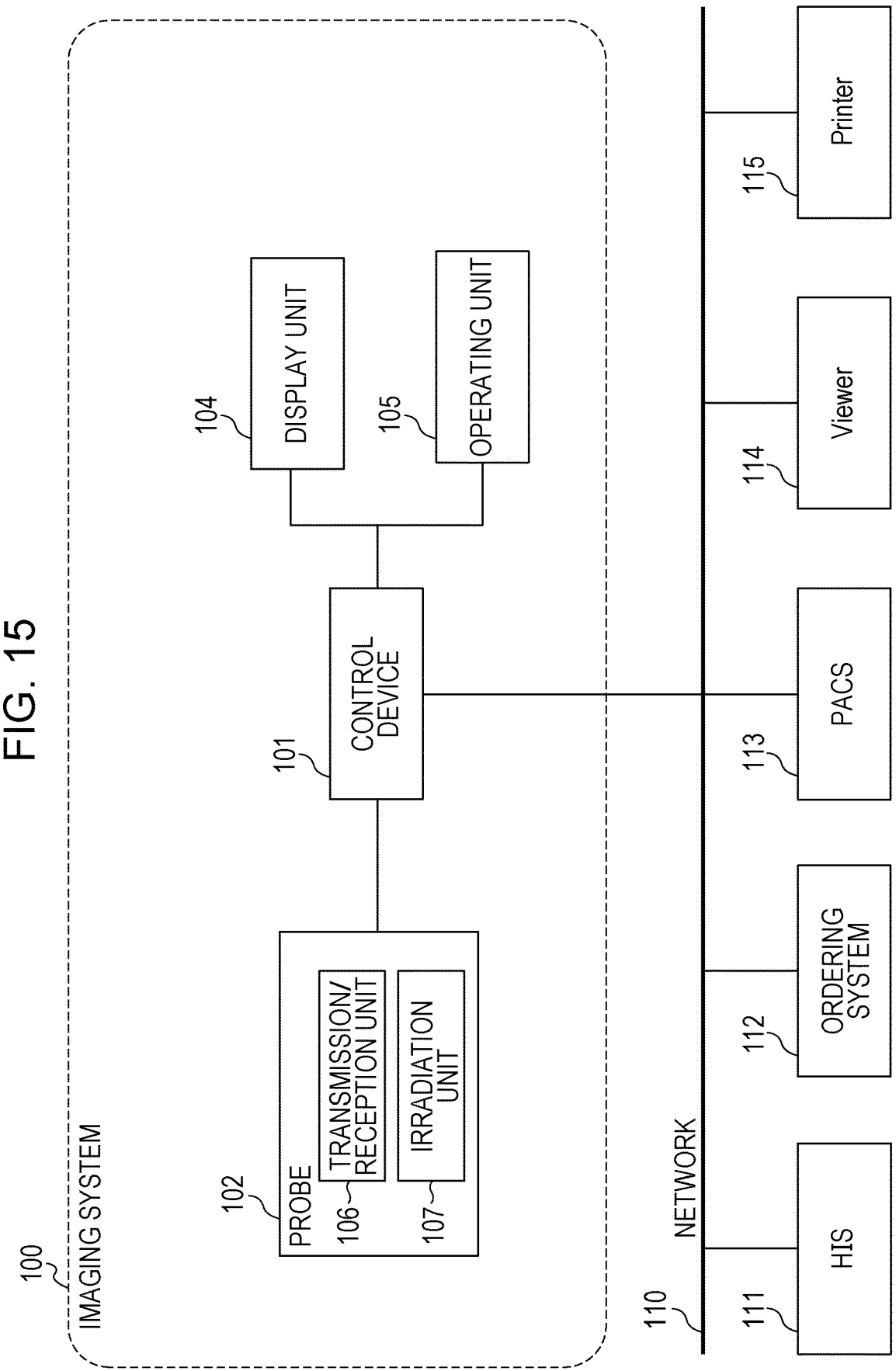

CONTROL DEVICE, CONTROL METHOD, CONTROL SYSTEM, AND NON-TRANSITORY RECORDING MEDIUM FOR SUPERIMPOSE DISPLAY

CROSS-REFERENCE TO RELATED APPLICATIONS

This application is a Continuation of International Patent Application No. PCT/JP2017/034989, filed Sep. 27, 2017, which claims the benefit of Japanese Patent Application No. 2016-198893, filed Oct. 7, 2016, both of which are hereby incorporated by reference herein in their entirety.

TECHNICAL FIELD

The present invention relates to a control device, a control method, a control system, and a program.

BACKGROUND ART

Ultrasound imaging devices and photoacoustic imaging devices are used as imaging devices for minimally-invasive imaging of states within the body of a subject of examination. For example, PTL 1 discloses generating a superimposed image where a photoacoustic image is superimposed on an ultrasound image in diagnosis using medical images.

CITATION LIST

Patent Literature

PTL 1 Japanese Patent Laid-Open No. 2005-21380

In a case where a superimposed image is generated at a certain device, and multiple medical images included in the superimposed image are transmitted to a viewer provided outside of this device, the external viewer has no information on how to superimpose the multiple medical images, and accordingly cannot generate a superimposed image. That is to say, there has been a problem in that some viewers cannot generate superimposed images.

SUMMARY OF INVENTION

A control device according to an embodiment of the present invention includes acquiring means configured to acquire a plurality of images including an ultrasound image and a photoacoustic image taken in an examination, selecting means configured to select, from the acquired plurality of images, a first image, and a second image to be displayed superimposed on the first image, based on information relating to the examination, and generating means configured to generate an object for outputting, to an external device, at least information for displaying the second image superimposed on the first image.

Further features of the present invention will become apparent from the following description of exemplary embodiments with reference to the attached drawings.

BRIEF DESCRIPTION OF DRAWINGS

FIGS. 6A and 6B are a flowchart illustrating an example of processing performed by the control device according to the embodiment of the present invention.

FIG. 9 is a diagram illustrating an example of a screen displayed on a display unit by the control device according to the embodiment of the present invention.

FIG. 14A is a diagram illustrating an example of a screen displayed on a display unit by the control device according to the embodiment of the present invention.

FIG. 14B is a diagram illustrating an example of a screen displayed on a display unit by the control device according to the embodiment of the present invention.

FIG. 15 is a diagram illustrating an example of the configuration of a system including the control device according to the embodiment of the present invention.

DESCRIPTION OF EMBODIMENTS

Figure 1:
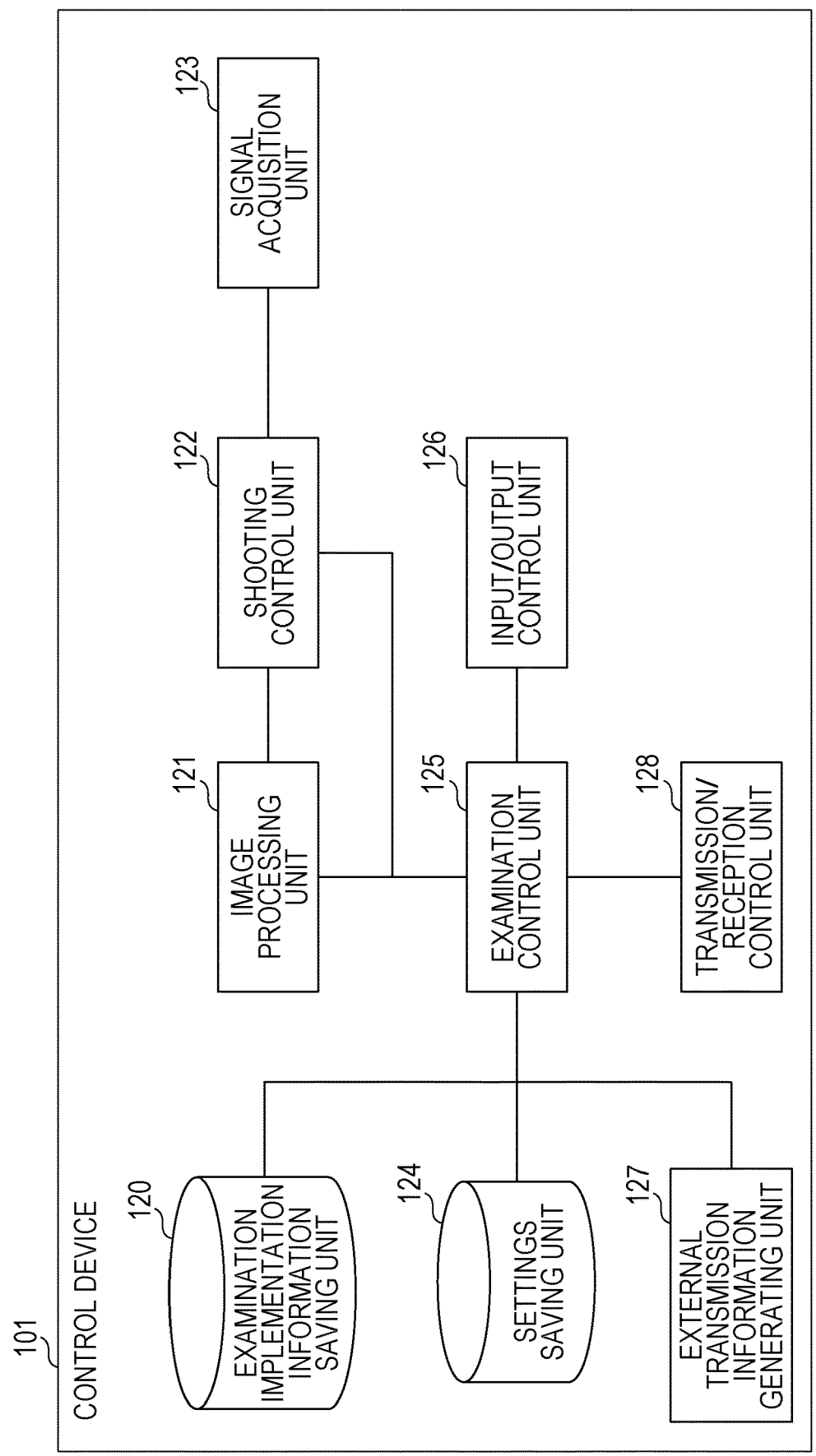
FIG. 1 is a diagram illustrating an example of the functional configuration of a control device according to an embodiment of the present invention.

An embodiment of the present invention will be described below with reference to the drawings. In the present specifications, acoustic waves generated by expansion occurring in the body of a subject of examination due to the subject body being irradiated by light are referred to as photoacoustic waves. Also, acoustic waves transmitted from a transducer, and reflected waves (echo) where the transmitted acoustic waves are reflected in the body of the subject of examination, are referred to as ultrasound waves.

Imaging methods using ultrasound and techniques of imaging using photoacoustic waves are being used as methods for minimally-invasive imaging of states inside the body of a subject of examination. The method of imaging using ultrasound is a method where ultrasound waves emitted from a transducer, for example, are reflected at tissues inside the body of the subject due to difference in acoustic impedance, and an image is generated based on the time for reflected waves to arrive at the transducer, and the intensity of the reflective waves. An image made by imaging using ultrasound waves will be referred to hereinafter as an ultrasound image. The user operates a probe while changing the angle and so forth, and can observe ultrasound images of various types of cross-sections in real-time. Ultrasound images visualize shapes of organs and tissue, and is being used to discover tumors and so forth. The method of imaging using photoacoustic waves is a method where an image is generated based on photoacoustic waves generated by thermal expansion of tissue within the body of the subject that has been irradiated by light, for example. An image where imaging has been performed using photoacoustic waves will be referred to hereafter as a photoacoustic image.

Photoacoustic images visualize information relating to optical properties, such as the degree of absorption of light by the tissues. It is known that blood vessels can be visualized by photoacoustic images due to optical properties of hemoglobin, for example, and studies are being made for use in evaluation of malignancy of tumors or the like.

There are cases where various types of information are collected by imaging the same part of the body of a subject based on different principles, in order to improve the accuracy of diagnosis. For example, there are cases where diagnosis regarding cancer is performed by combining form information obtained by computed tomography (CT) images and functional information related to metabolism obtained from positron-emission tomography (PET) images. It is thought that performing diagnosis using information obtained by imaging different phenomena based on different principles is effective in improving accuracy of diagnosis.

Imaging devices for obtaining images that combine the properties of the above-described ultrasound images and photoacoustic images are being studied. Particularly, both ultrasound images and photoacoustic images are imaged using ultrasound waves from the body of the subject, so imaging of ultrasound images and photoacoustic images can be performed using the same imaging device. More specifically, reflected waves that the subject body has been irradiated by and photoacoustic waves can be received at the same transducer. Accordingly, ultrasound wave signals and photoacoustic signals can be acquired at a single probe, so an imaging device that performs imaging of ultrasound images and imaging of photoacoustic images can be realized with the same device, without the hardware configuration becoming complicated.

For example, in a case of performing examination using an imaging device that performs imaging of ultrasound images and imaging of photoacoustic images as described above, it is envisioned that various images will be generated during a single examination. An example of a case will be described where imaging of ultrasound images is being performed, and in conjunction with this, imaging of photoacoustic images is performed by the user performing input of instructions instructing irradiation by light as appropriate. A moving image made up of a group of a series of ultrasound images, or ultrasound images at timings instructed by the user, are generated in a single examination. Each time the body of the subject is irradiated by light in a single examination, photoacoustic waves are generated in the body, and various types of photoacoustic images are generated which will be described later. In a case where irradiation by light is performed multiple times in a single examination, multiple photoacoustic images can be generated at each timing of irradiation by light.

In a case where images are transmitted to an external device as individual objects, there is concern that superimposed display cannot be made depending on the specifications of the viewer, and further, the user has to set the form of the superimposed display manually. Alternatively, in a case where a composited image in which multiple images have been composited is transmitted to the external device as a single object, the user can observe in a state where the multiple images have been composited, but cannot display each of the multiple images individually on the viewer.

In light of these problems, it is preferable, from the perspective of performing observation while comparing ultrasound images and photoacoustic images, to store ultrasound images and photoacoustic images imaged at generally the same time in a correlated manner. Further, at the time of outputting a correlated image group to an external device, it is preferable that an automatically displayable object be generated and output in a form suitable for the user.

A control device according to an embodiment of the present invention is provided to improve the workflow efficiency of interpreting and diagnosing, for example, by generating an object at an external device where multiple images can be displayed to the user in a suitable form.

FIG. 15 is a diagram illustrating an example of the configuration of a system including a control device 101 according to the embodiment of the present invention. The imaging system 100 that is capable of generating ultrasound images and photoacoustic images is connected to various types of external devices via a network 110. The configurations included in the imaging system 100 and the various types of external devices do not have to be installed within the same facilities, and it is sufficient for these to be communicably connected.

The imaging system 100 includes a control device 101, a probe 102, a display unit 104, and an operating unit 105. The imaging control device 101 is a device that acquires ultrasound wave signals and photoacoustic signals from the probe 102, control acquisition of the photoacoustic signals based on the ultrasound signals for example, and generates photoacoustic images based on this control. The control device 101 also acquires information relating to examinations including ultrasound images and photoacoustic images from an ordering system 112, and controls the probe 102 and display unit 104 when the examination is performed. The control device 101 outputs generated ultrasound images, photoacoustic images, and superimposed images where photoacoustic images have been superimposed on ultrasound images, to a picture archiving and communication system (PACS) 113. The control device 101 exchanges information with external devices such as the ordering system 112 and PACS 113, in accordance with standards such as Health Level 7 (HL7) and Digital Imaging and Communications in Medicine (DICOM). Details of processing performed by the control device 101 will be described later.

Examples of regions in the body of the subject of examination regarding which ultrasound images are to be taken by the imaging system 100 include the cardiovascular region, breasts, liver, pancreas, abdomen, and so forth. The imaging system 100 may also take ultrasound images of the subject body where a microbubble-based ultrasound contrast agent has been administered, for example.

Examples of regions in the body of the body of the subject of examination regarding which photoacoustic images are to be taken by the imaging system 100 are regions such as the cardiovascular region, breasts, cervical region, abdomen, the extremities including fingers and toes, and so forth. Particularly, new blood vessels and blood vessel regions including plaque on vascular walls may be the object of taking photoacoustic images, in accordance with characteristics regarding light absorption within the subject body. Although an example will be described below regarding a case of taking photoacoustic images while taking ultrasound image, the region on the body of the subject where photoacoustic images are being taken by the imaging system 100 does not necessarily have to agree with the region where ultrasound images are being taken. Dyes such as methylene blue, indocyanine green, fine gold particles, and substances where these have been aggregated or chemically modified may be used as a contrast agent in the imaging system 100, and administered to the subject for imaging of photoacoustic images.

The probe 102 is operated by the user and transmits ultrasound wave signals and photoacoustic signals to the control device 101. The probe 102 includes a transmission/reception unit 106 and an irradiation unit 107. The probe 102 transmits ultrasound waves from the transmission/reception unit 106, and receives the reflected waves at the transmission/reception unit 106. The probe 102 irradiates the subject by light from the irradiation unit 107, and receives the photoacoustic waves at the transmission/reception unit 106. The probe 102 converts the received reflected waves and photoacoustic waves into electrical signals, and transmits to the control device 101 as ultrasound wave signals and photoacoustic signals. The probe 102 is preferably controlled so as to execute transmission of ultrasound waves for acquiring ultrasound wave signals and irradiation by light to acquire photoacoustic signals when information is received that contact has been made with the subject body.

The transmission/reception unit 106 includes at least one transducer (omitted from illustration), a matching layer (omitted from illustration), a damper (omitted from illustration), and an acoustic lens (omitted from illustration). The transducer (omitted from illustration) is formed of a material that exhibits the piezoelectric effect, such as lead zirconate titanate (PZT) or polyvinylidene difluoride (PVDF). The transducer (omitted from illustration) may be other than a piezoelectric element, and may be a capacitive transducer (capacitive micro-machined ultrasonic transducer (CMUT)) or a transducer using a Fabry-Perot interferometer, for example. Typically, ultrasound wave signals are 2 to 20 MHz and photoacoustic signals are 0.1 to 100 MHz in frequency component, so an arrangement that can detect these frequencies is used for the transducer (omitted from illustration). The signals obtained by the transducer (omitted from illustration) are time-division signals. The amplitude of the received signals represents values based on acoustic pressure received at the transducer at each time. The transmission/reception unit 106 includes a circuit (omitted from illustration) for electronic focus or a control unit. The layout of the transducer (omitted from illustration) is a sector array, linear array, a convex array, an annular array, or a matrix array, for example. The probe 102 acquires ultrasound wave signals and photoacoustic signals, which may be acquired alternately, or acquired simultaneously or may be acquired according to a preset form.

The transmission/reception unit 106 may have an amplifier (omitted from illustration) that amplifies time-sequence analog signals that the transducer (omitted from illustration) has received. The transmission/reception unit 106 may also have an A/D converter that convers time-sequence analog signals that the transducer (omitted from illustration) has received into time-sequence digital signals. The transducer (omitted from illustration) may be divided into a transmitting portion and a receiving portion in accordance with the purpose of imaging the ultrasound image. The transducer (omitted from illustration) may also be divided into a portion for imaging ultrasound images and a portion for imaging photoacoustic images.

The irradiation unit 107 includes a light source (omitted from illustration) for acquiring photoacoustic signals and an optical system (omitted from illustration) that guides pulse light emitted from the light source (omitted from illustration) to the subject. The pulse width of light emitted from the light source (omitted from illustration) is a pulse width of 1 ns or longer to 100 ns or shorter, for example. The wavelength of the light that the light source (omitted from illustration) emits is a wavelength of 400 nm or longer to 1600 nm or shorter, for example. In a case of imaging blood vessels near the surface of the subject with high resolution, a wavelength of 400 nm or longer to 700 nm or shorter, where the absorption at blood vessels is great, is preferable. In a case of imaging deep portions of the body of the subject, a wavelength of 700 nm or longer to 1100 nm or shorter, that is not readily absorbed by water or tissue such as fat, is preferable.

The light source (omitted from illustration) is a laser or light-emitting diode, for example. A light source where wavelength can be changed may be used as the irradiation unit 107, in order to acquire photoacoustic signals using light of multiple wavelengths. Alternatively, the irradiation unit 107 may be of a configuration having multiple light sources that emit light of different wavelengths from each other, where irradiation can be alternately performed by light of different wavelengths from the different light sources. Examples of laser include solid-state laser, gas laser, dye laser, and semiconductor laser. A pulsed laser such as an Nd:YAG laser or an alexandrite laser may be used for the light source (omitted from illustration). Also, a Ti-sapphire laser or optical parametric oscillator (OPO) laser that uses Nd:YAG laser light as excitation light may be used as the light source (omitted from illustration). Further, a microwave source may be used as the light source (omitted from illustration).

Optical elements such as lenses, mirrors, optical fibers, and so forth, are used as the optical system (omitted from illustration). Irradiation is preferably performed with the beam diameter of the pulsed light expanded in a case where the subject is a breast, so a diffraction plate for diffracting the emitted light may be provided to the optical system (omitted from illustration). Alternatively, a configuration may be made where the optical system (omitted from illustration) has lenses or the like and can carry out beam focusing, in order to raise resolution.

The display unit 104 displays images imaged by the imaging system 100 and information relating to the examination, based on control from the control device 101. The display unit 104 provides an interface to accept user instructions, based on control from the control device 101. An example of the display unit 104 is a liquid crystal display.

The operating unit 105 transmits information relating to input of user operations to the control device 101. The operating unit 105 is, for example, a keyboard or trackball, or various types of buttons for performing input of operations relating to examination.

The display unit 104 and operating unit 105 may be integrated as a touch panel display. There is no need for the control device 101, display unit 104, and operating unit 105 to be separate devices, and these configurations may be realized as an integrated console. The control device 101 may have multiple probes.

A hospital information system (HIS) 111 is a system that supports hospital operations. The HIS 111 includes an electronic health record system, an ordering system, and an medical accounting system. The HIS 111 enables comprehensive management from ordering examinations up to accounting. The ordering system of the HIS 111 transmits order information to ordering systems 112 of respective departments. Implementation of the order is managed at the ordering system 112 described later.

The ordering system 112 is a system that manages examination information, and manages progress of each examination at the imaging device. An ordering system 112 may be configured for each department that performs examination. An example of the ordering system 112 is, in the case of a radiology department, a radiology information system (RIS). The ordering system 112 transmits information for examinations to be performed at the imaging system 100 to the control device 101, in response to a query from the control device 101. The ordering system 112 receives information relating to progress of examinations from the control device 101. Upon having received information from the control device 101 to the effect that an examination has been completed, the ordering system 112 transmits information indicating that this examination has been completed to the HIS 111. The ordering system 112 may be integrated with the HIS 111.

A picture archiving and communication system (PACS) 113 is a database system that stores images obtained at various types of imaging devices inside of and outside of the facilities. The PACS 113 has a storage unit (omitted from illustration) that stores medical images and imaging conditions of the medical images, supplementary information such as parameters of image processing including reconfiguration, patient information, and so forth, and a controller (omitted from illustration) that manages information stored in this storage unit. The PACS 113 stores ultrasound images, photoacoustic images, and superimposed images, which are objects output form the control device 101. Communication between the PACS 113 and the control device 101, and various types of images stored in the PACS 113, preferably conform to standards such as HL7 and DICOM. Various types of images output from the control device 101 are correlated with supplementary information in various types of tags in accordance with the DICOM standard, and stored.

A viewer 114 is an image diagnosis terminal, that reads out images stored in the PACS 113 or the like, and displays for diagnosis. A physician displays images on the viewer 114 and observes the images, and records information obtained as a result of this observation as an image diagnosis report. Image diagnosis reports created using the viewer 114 may be stored in the viewer 114, or may be output to the PACS 113 or a report server (omitted from illustration) and stored.

A printer 115 prints images stored in the PACS 113 or the like. An example of the printer 115 is a film printer, that outputs images stored in the PACS 113 or the like by printing on film.

Figure 2:
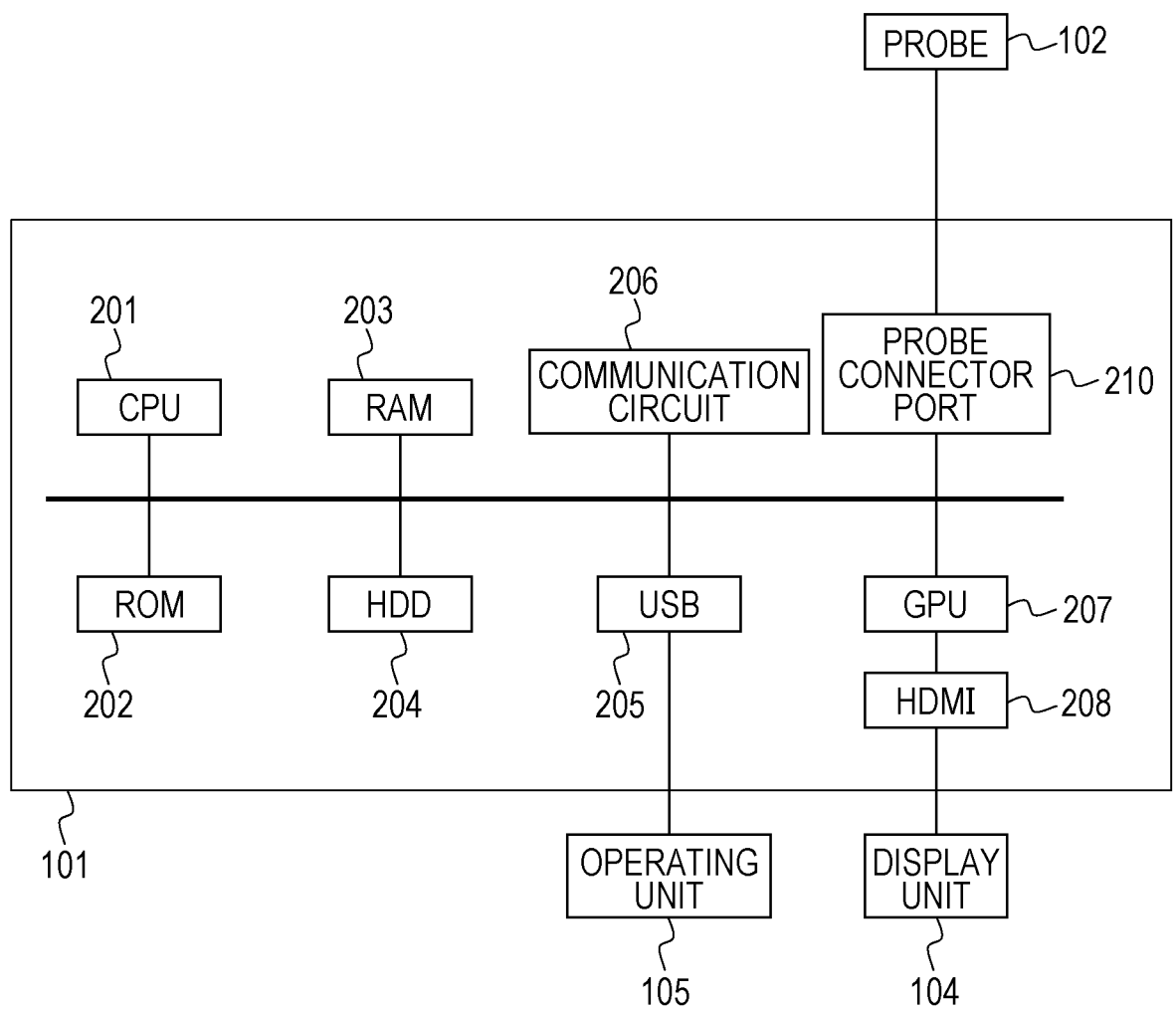
FIG. 2 is a diagram illustrating an example of the hardware configuration of the control device according to the embodiment of the present invention.

FIG. 2 is a diagram illustrating an example of the configuration of the control device 101. The control device 101 includes a central processing unit (CPU) 201, read-only memory (ROM) 202, random access memory (RAM) 203, a hard disk drive (HDD) 204, a Universal Serial Bus (USB) port 205, a communication circuit 206, a graphics processing unit (GPU) 207, a High-Definition Multimedia Interface (HDMI, a registered trademark) port 208, and a probe connector port 210. These components are communicably connected by a bus. The bus is a database that is used for exchanging data among the hardware connected thereto, and for transmitting commands from the CPU 201 to other hardware.

The CPU 201 is a control circuit that centrally controls the control device 101 and components connected thereto. The CPU 201 carries out control by executing programs stored in the ROM 202. The CPU 201 also runs a display driver that is software for controlling the display unit 104, and performs display control of the display unit 104. The CPU 201 further performs input/output control of the operating unit 105.

The ROM 202 stores programs and data recording procedures for control by the CPU 201. The ROM 202 stores a boot program for the control device 101 and various types of initialization data. The ROM 202 also stores various types of programs for realizing the processing by the control device 101.

The RAM 203 provides a workspace storage region for the CPU 201 to perform control by control programs. The RAM 203 has stack and work regions. The RAM 203 stores programs that the control device 101 and components connected thereto executing the processing of, and various types of parameters used in image processing. The RAM 203 stores control programs executed by the CPU 201, and temporarily stores various types of data for the CPU 201 to execute various types of control.

The HDD 204 is an auxiliary storage device for saving various types of data, such as ultrasound images, photoacoustic images, and so forth.

The USB port 205 is a connector to connect to the operating unit 105.

The communication circuit 206 is a circuit for performing communication with components making up the imaging system 100, and various types of external devices connected to the network 110. The communication circuit 206 stores information to be output in the form of transmission packets, and outputs to external devices via the network 110 by communication technology such as TCP/IP, for example. The control device 101 may have multiple communication circuits in accordance with desired communication forms.

The GPU 207 is included in a general-purpose graphics board having video memory. The GPU 207 performs reconstruction processing of photoacoustic images, for example. Using this sort of processing unit enables processing such as reconstruction to be performed at high speeds without requiring dedicated hardware.

The HDMI (registered trademark) port 208 is a connector for connecting to the display unit 104.

The probe connector port 210 is a port for connecting the probe 102 to the control device 101. The ultrasound wave signals and photoacoustic signals output from the probe 102 are acquired by the control device 101 via the probe connector port 210.

The CPU 201 and GPU 207 are examples of a processor. The ROM 202, RAM 203, and HDD 204 are examples of memory. The control device 101 may have multiple processors. In a first embodiment, the functions of components of the control device 101 are realized by the processor of the control device 101 executing programs stored in memory.

Note that the control device 101 may have a CPU or GPU that performs particular processing in a dedicated manner. The control device 101 may also have a field-programmable gate array (FPGA) where particular processing or all processing has been programmed. The control device 101 may have a solid state drive (SSD) as an auxiliary storage device.

FIG. 1 is a diagram illustrating an example of the functional configuration of the control device 101. The control device 101 includes an examination implementation information saving unit 120, an image processing unit 121, a imaging control unit 122, a signal acquisition unit 123, a settings saving unit 124, an examination control unit 125, an input/output control unit 126, an external transmission information generating unit 127, and a transmission/reception control unit 128.

The examination implementation information saving unit 120 stores information of examinations carried out in the past. Examination information stored in the examination implementation information saving unit 120 is registered, updated, deleted, and searched, based on input of user operations and control from configurations related to the control device 101. The examination implementation information saving unit 120 is made up of a database.

The image processing unit 121 generates ultrasound images and photoacoustic images, and superimposed images where photoacoustic images have been superimposed on ultrasound images. The image processing unit 121 generates ultrasound images to be displayed on the display unit 104 from ultrasound wave signals acquired from the signal acquisition unit 123. The image processing unit 121 generates ultrasound images appropriate for the mode that has been set, based on information of imaging procedures acquired from the examination control unit 125. For example, in a case where the Doppler mode is set as the imaging procedure, the image processing unit 121 generates an image indicating flow rate within the subject body, based on the difference between the frequency of ultrasound wave signals acquired by the signal acquisition unit 123 and the transmission frequency.

The image processing unit 121 also generates photoacoustic images based on photoacoustic signals acquired by the signal acquisition unit 123. The image processing unit 121 reconstructs distribution of photoacoustic waves when irradiated by light (hereinafter referred to as initial acoustic pressure distribution), based on photoacoustic signals. The image processing unit 121 acquires a distribution of coefficients of light absorption in the subject body, by dividing the initial acoustic pressure that has been reconstructed by the light fluence distribution in the subject body of the light that the subject body has been irradiated by. A concentration distribution of matter in the subject body is also acquired from distribution of coefficients of light absorption as to multiple wavelengths, using the fact that the degree of absorption of light within the body differs in accordance with the wavelength of light that the body is irradiated by. For example, the image processing unit 121 acquires the distribution of matter in the subject body regarding oxyhemoglobin and deoxyhemoglobin. The image processing unit 121 further acquires oxygen saturation distribution as a ratio of oxyhemoglobin concentration as to deoxyhemoglobin concentration. Photoacoustic images generated by the image processing unit 121 are images indicating information such as the above-described initial acoustic pressure distribution, light fluence distribution, absorption coefficient distribution concentration distribution of matter, and oxygen saturation distribution.

The image processing unit 121 further composites data of multiple images, and generates a single composite image. For example, an image where a photoacoustic image has been superimposed on an ultrasound image is generated as a composite image. Hereinafter, an image that serves as the background of a superimposed display will be referred to as a base image, and an image superimposed on the base image as a layer image. The image that is being displayed superimposed will be referred to as a superimposed image. The image processing unit 121 performs image processing for display and diagnosis assistance on the image data, such as gradient processing. The image processing unit 121 is an example of acquisition means for acquiring ultrasound images and photoacoustic images.

The imaging control unit 122 controls the probe 102 based on information of imaging procedures received from the examination control unit 125. The imaging control unit 122 transmits information relating to the examination order including information of the imaging procedure to the signal acquisition unit 123. The imaging control unit 122 controls the flow relating to acquisition of ultrasound wave signals and acquisition of photoacoustic signals in the examination.

The signal acquisition unit 123 obtains ultrasound wave signals and photoacoustic signals from the probe 102. Specifically, the signal acquisition unit 123 acquires ultrasound wave signals and photoacoustic signals from information acquired from the probe 102, while distinguishing between the two, based on information from the examination control unit 125 and the imaging control unit 122. For example, there are cases where the timing of acquisition of ultrasound wave signals and photoacoustic signals is stipulated in the imaging procedure being used for imaging. In this case, the signal acquisition unit 123 acquires ultrasound wave signals and photoacoustic signals from information acquired from the probe 102, based on the acquisition timing information acquired from the examination control unit 125, while distinguishing between the two.

The settings saving unit 124 stores information of setting relating to actions of the control device 101, such as imaging procedure information 301, failed shot information, and so forth. For example, the settings saving unit 124 accepts and stores setting relating to generating of an object for superimposed display of image data acquired by the imaging system 100 at an external device. The information of the settings stored in the settings saving unit 124 is registered updated, deleted, and searched, based on input of user operations and control from configurations related to the control device 101. Details of information of settings stored in the settings saving unit 124 will be described later. The settings saving unit 124 is made up of a database. The settings saving unit 124 is an example of accepting means.

The examination control unit 125 controls examinations performed by the imaging system 100. The examination control unit 125 acquires information of examination orders from the ordering system 112. Examination orders include information of the patient to be examined, and information relating to the imaging procedure. The examination control unit 125 transmits information relating to the examination order to the imaging control unit 122. The examination control unit 125 also displays information of the examination on the display unit 104 via a display control unit (omitted from illustration), to present information relating to the examination to the user. Information of the examination that is displayed on the display unit 104 includes information of the patient to be examined, information of imaging procedures involved in the examination, and images that have already been imaged and generated. The examination control unit 125 further transmits information relating to the progress of the examination to the ordering system 112. For example, when the examination is started by the user, the examination control unit 125 notifies the ordering system 112 of the start, and when imaging by all imaging procedures included in the examination is completed, notifies the ordering system 112 of the completion.

The input/output control unit 126 controls the display unit 104 to display information on the display unit 104. The input/output control unit 126 displays information on the display unit 104 in accordance with input from the examination control unit 125 and image processing unit 121, and input of user operations via the operating unit 105. The input/output control unit 126 also acquires information from the operating unit 105.

The external transmission information generating unit 127 generates information for transmitting various types of information to external devices such as the PACS 113 and viewer 114, in accordance with control from the examination control unit 125 and input of user operations. For example, the external transmission information generating unit 127 generates information to output ultrasound images and photoacoustic images generated at the image processing unit 121, and superimposed images thereof, to the PACS 113. In formation output to external devices include supplemental information supplemented as various types of tags following the DICOM standard. The supplemental information includes patient information, information indicating the imaging device that has imaged this image, image ID for uniquely identifying the image, and examination ID for uniquely identifying the examination where the image was imaged. The supplemental information also includes information correlating ultrasound images and photoacoustic images imaged during the examination. Information correlating ultrasound images and photoacoustic images is information indicating, out of multiple frames making up ultrasound images for example, a frame that is the closest to the timing of having acquired a photoacoustic image. That is to say, the external transmission information generating unit 127 generates objects for transmission to external devices based on information stored in the examination implementation information saving unit 120 and settings saving unit 124, and the ultrasound images and photoacoustic images acquired at the image processing unit 121. Objects are information that are the object of transmission from the control device 101 to external devices such as the PACS 113 and viewer 114. Objects generated by the external transmission information generating unit 127 include information for displaying a certain image superimposed on another image, at least. There are cases where the object is configured of image data and supplemental information regarding that image data. The external transmission information generating unit 127 generates, for example, external transmission information 1101. Details of external transmission information 1101 will be described later. The external transmission information generating unit 127 is an example of generating means. The external transmission information generating unit 127 is also an example of selecting means.

The transmission/reception control unit 128 controls transmission and reception of information among external device such as the ordering system 112, PACS 113, and viewer 114, and the control device 101, via the network 110. The transmission/reception control unit 128 receives information of examination orders from the ordering system 112. The transmission/reception control unit 128 transmits objects generated at the external transmission information generating unit 127 to the PACS 113 and viewer 114.

Note that FIGS. 1, 2, and 15 illustrate an example where the control device 101 is connected to the probe 102 and controls imaging of ultrasound images and photoacoustic images, but the control device according to an embodiment of the present invention is not necessarily restricted to this form. The control device according to the embodiment of the present invention may have a configuration where ultrasound images and photoacoustic images are acquired from a device that controls the imaging.

Figure 3:
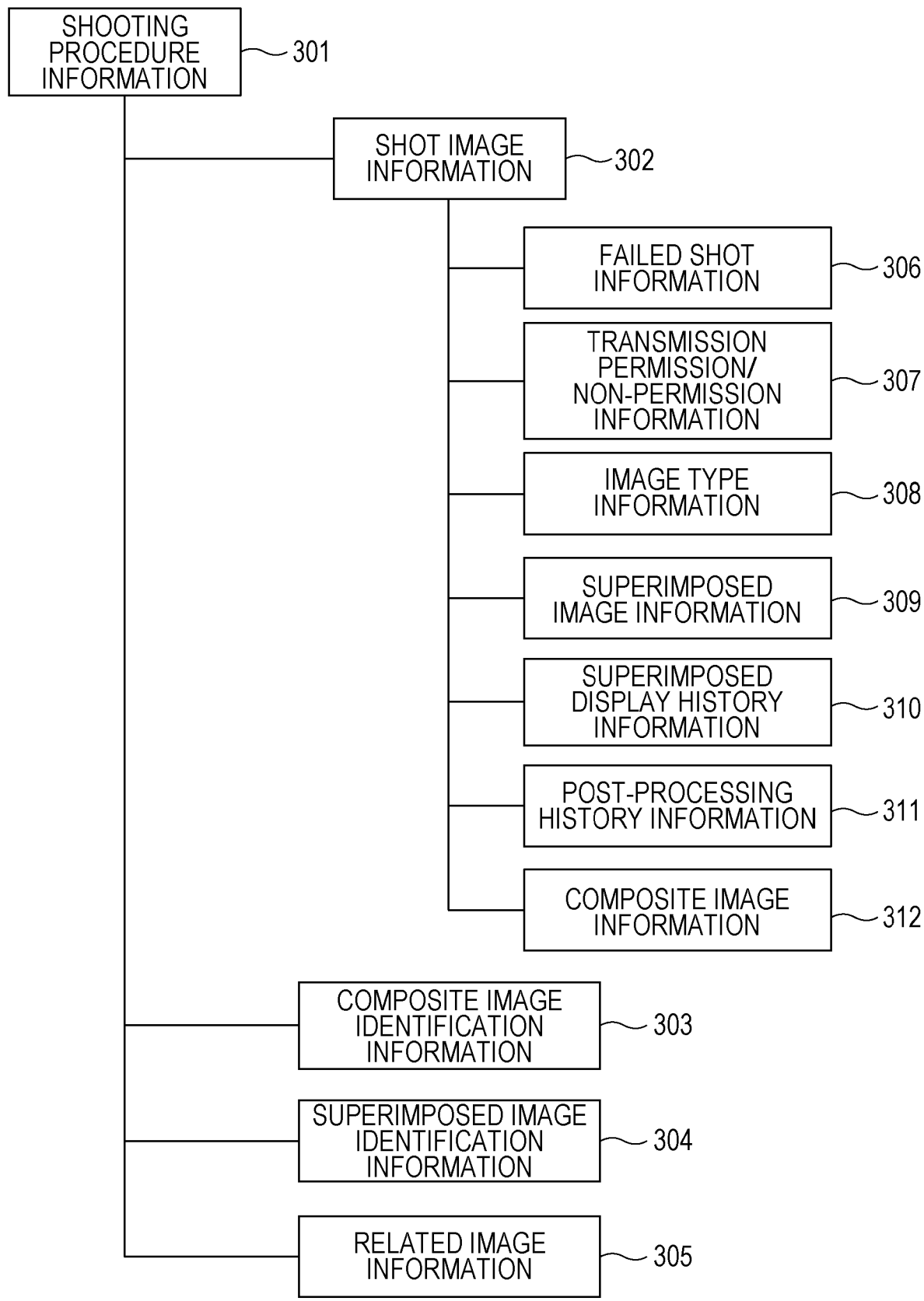
FIG. 3 is a diagram illustrating an example of information generated by the control device according to the embodiment of the present invention.

FIG. 3 is a diagram illustrating the configuration of imaging procedure information 301 generated by the examination control unit 125 based on the examination order received from the ordering system 112. The imaging procedure information 301 is used to acquire ultrasound images and photoacoustic images, and generate objects for output to external devices at the external transmission information generating unit 127. This will be described in detail below.

The imaging procedure information 301 includes, for example, shot image information 302, composite image identification information 303, superimposed image identification information 304, and related image information 305. The imaging procedure information 301 may further include information indicating a imaging procedure ID uniquely identifying the imaging procedure information 301, imaging type, imaging site, and imaging direction, default setting values of reconstruction parameters and imaging conditions, storage transfer settings, print output settings, and so forth. That is to say, the imaging procedure information 301 is information for implementing imaging, subjecting image data to post-processing and transmitting to an external device, and includes information that can be set for individual imaging procedures.

The shot image information 302 is made up of the image data imaged by the imaging system 100, and supplemental information supplementing this image data. In the present embodiment, the shot image information 302 and image data correspond one on one. For example, in a case where there is a plurality of image data imaged by the same imaging procedure in an examination, a plurality of shot image information 302 will be included in the imaging procedure information 301.

The composite image identification information 303 includes image data of a composite image wherein at least two or more image data out of the shot image information 302 included in the imaging procedure information 301 have been composited in an overlaid state to obtain a single image data, and supplemental information. Composite image identification information 303 of a count corresponding to the number of composite images created using the image data imaged by the same imaging procedure are registered in the imaging procedure information 301. Supplemental information of the composite image identification information 303 includes an image ID uniquely identifying the composite image identification information 303, respective image IDs for identifying each of the images used to generate this composite image, superimposing method, and so forth.

The superimposed image identification information 304 is information for identifying, out of the shot image information 302 included in the imaging procedure information 301, an object displayable as a superimposed image. The superimposed image identification information 304 is registered in the imaging procedure information 301 in accordance of the number of objects displayable as superimposed images, created using the image data imaged by the same imaging procedures. The superimposed image identification information 304 is information for managing groups of imaged images to be used for superimposed display, for example, and includes an object ID for identifying an object displayable as a superimposed image. The superimposed image identification information 304 may further include information of image IDs for identifying at least two or more of image data included in this object.

The related image information 305 is information for handling multiple image data that has been shot in the imaging procedure information 301 as a correlated group. The related image information 305 includes a group ID for identifying the group, and information of combinations of at least two or more image IDs group following rules for correlation that have been decided beforehand, for example. Examples of rules for correlation include correlating an image information group including time of irradiation of the subject body by light or ultrasound waves, and signal detection time, within a predetermined range of time. Accordingly, a photoacoustic image generated based on photoacoustic waves generated by a single irradiation by light, and an ultrasound image identified based on the time of irradiation by light, can be grouped.

The shot image information 302 includes, for example, failed shot information 306, transmission permission/non-permission information 307, image type information 308, superimposed image information 309, superimposed display history information 310, post-processing history information 311, and composite image information 312. The shot image information 302 further includes an image ID that uniquely identifies the shot image information 302, image data, image processing parameters, geometric transform parameters, placement information, information of region of interest, implemented imaging conditions, and implemented imaging information. The image processing parameters include reconstruction parameters regarding reconstruction of photoacoustic images, for example. Implementation imaging conditions are the actual imaging conditions at the time of implementing imaging. Implementation imaging information includes information of the time of acquiring the image, and image ID of correlated image information, for example. Placement information is information for supplemental information for superimposed display on image data, including such as free annotation, marker indicating imaging direction, measurement processing, cropping, masking, and so forth.

The failed shot information 306 is information indicating whether the image data corresponding to the shot image information 302 is a so-called failed-shot image that is not suitable for diagnosis. In a case where the image data corresponding to the shot image information 302 is a failed-shot image, information indicating the reason for the failed shot is included in the failed shot information 306.

The transmission permission/non-permission information 307 is information indicating whether or not to transmit image data corresponding to the shot image information 302 to an external device.

The image type information 308 is information for identifying the type of image data corresponding to the shot image information 302. The image type information 308 includes information relating to, for example, imaging method of the image data, image type, and positioning. Information of the image type is information indicating the type of image generated based on ultrasound wave signals, and information indicating the type of image generated based on photoacoustic signals, for example. Examples of images generated based on ultrasound wave signals include B-mode images and elastography images. Examples of images generated based on photoacoustic signals include absorption coefficient images and oxygen saturation images.

Information of image type may further include information indicating whether the shot image information 302 is a form image or a functional image. The image type of the image data and information of whether a form image or a functional image may be set by input of user operations, or may be set based on information set beforehand. Information relating to positioning is information indicating whether or not the image has been deformed at the time of positioning for making a composited image or superimposed display.

The superimposed image information 309 is information relating to a superimposed image including image data corresponding to the shot image information 302.

The superimposed display history information 310 is information indicating whether, at the time of acquiring the image data corresponding to the shot image information 302, superimposed display with other image data was performed or not. In a case where superimposed display was performed, the image ID of the image data that was displayed superimposed and information indicating the superimposing order is recorded in the superimposed display history information 310, regardless of the superimposing order as to the other image data in the superimposed display.

The post-processing history information 311 is information indicating whether or not superimposed display with other image data was performed at the time of performing post-processing of the image data corresponding to the shot image information 302. In a case where superimposed display was performed, the image ID of the image data that was displayed superimposed and the superimposing order are recorded, regardless of the superimposing order as to the other image data in the superimposed display.

The composite image information 312 is information indicating a composited image in which the image data corresponding to the shot image information 302 is included.

In a case where waveform data such as A-mode based on ultrasound wave signals is generated for example, the imaging procedure information 301 includes information in the image type information 308 indicating that this is waveform data.

The imaging procedure information 301 illustrated in FIG. 3 is one example. Any data structure may be used as long as capable of generating and outputting to external devices objects that can be displayed in a display form suitable for the user, as described later, and not all of the above-described information has to be included.

Figure 4:
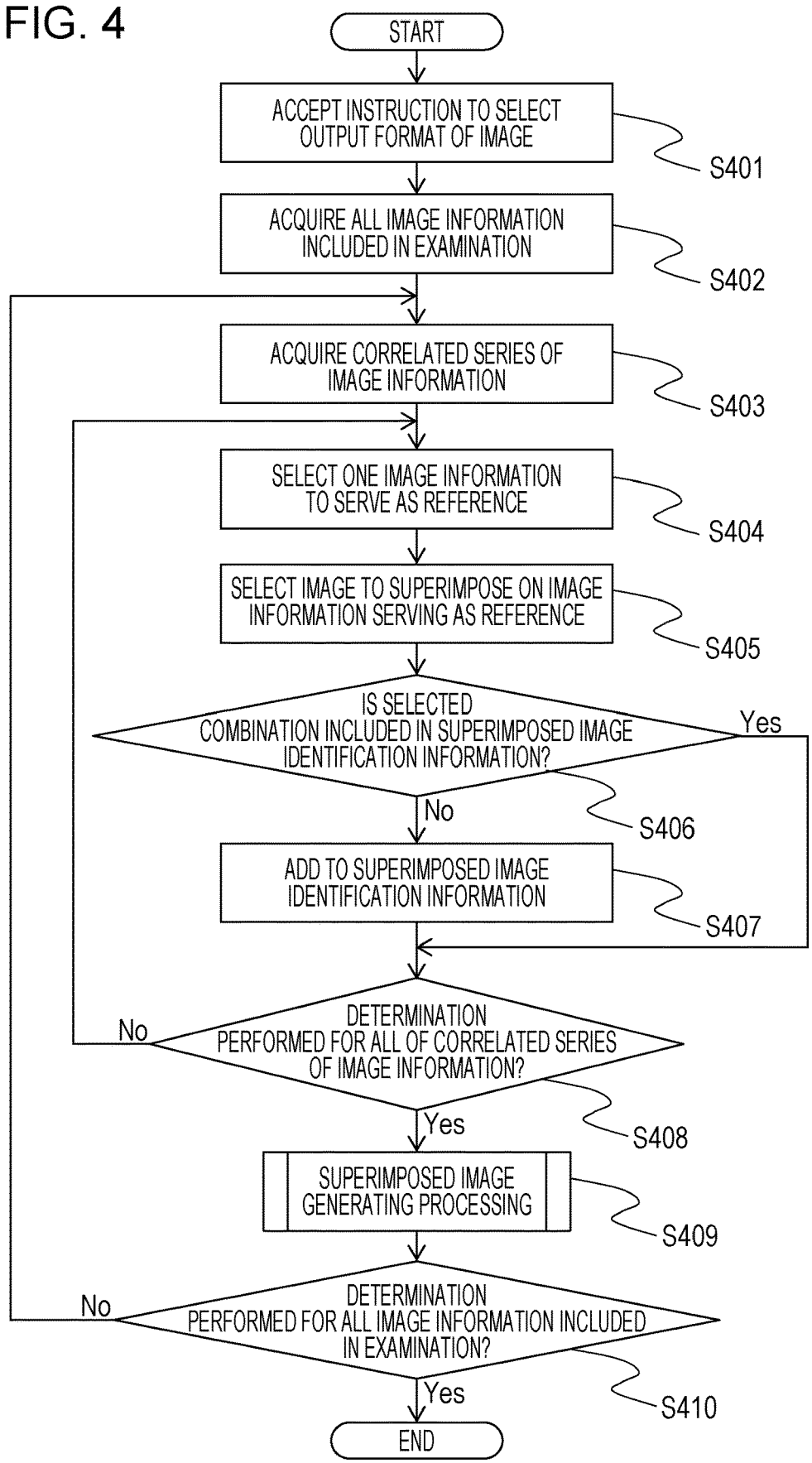
FIG. 4 is a flowchart illustrating an example of processing performed by the control device according to the embodiment of the present invention.

FIG. 4 is a flowchart illustrating an example of processing for selecting image data to be included in a superimposed image, for output of an object displayable as the superimposed image to an external device. In the following processing, the entity carrying out the processing in each step is the CPU 201 or the GPU 207, unless particularly stated otherwise.

In step S401, the examination control unit 125 accepts instruction selecting the output form of image data. Instruction of this selection is performed by input of user operations, or by control within the control device 101. An example of an instruction of this selection being made by internal control of the control device 101 is a notification indicating that irradiation by ultrasound waves and light has ended is notified from the signal acquisition unit 123 via the imaging control unit 122 to the examination control unit 125, thereby instructing this selection.

In step S402, the examination control unit 125 acquires shot image information corresponding to all image data acquired in the examination. For example, there are cases where, in the first examination, while generating ultrasound images in real time by intermittently irradiating the subject by ultrasound waves, the subject is irradiated by light at an optional timing to obtain photoacoustic signals and generate photoacoustic images. In this case, multiple photoacoustic images generated based on photoacoustic waves generated by each irradiation by light that is performed, and shot image information corresponding to ultrasound images identified based in information relating to the irradiation by light, are each acquired. Shot image information corresponding to a moving image made up of a series of ultrasound images generated in real time may be acquired.

In step S403, the examination control unit 125 acquires the series of shot image information that has been correlated. The series of shot image information that has been correlated is identified by the related image information 305 included in the imaging procedure information 301. Accordingly, the series of shot image information that has been correlated, including a photoacoustic image generated based on photoacoustic waves generated by a single irradiation by light, and a ultrasound image identified based on information relating to the irradiation by light, is acquired.

In step S404, the external transmission information generating unit 127 acquires one of image information to serve as a reference, out of the series of shot image information acquired in step S403. The image information to serve as a reference does not necessarily have to be the base image of a superimposed image. The image information to serve as a reference does not have to be included in an object for output to an external device. The examination control unit 125 transmits the imaging procedure information 301 to the external transmission information generating unit 127. The external transmission information generating unit 127 acquires information of settings relating to the selection, from the settings saving unit 124, for example. For example, image information corresponding to the image type that has the greatest number of image data in the series of image data acquired in the examination is taken as the reference. The user may perform settings beforehand to set a particular image type as the reference. In another example, the image type that is most suitable for observation of form information in the series of image data acquired in the examination may be taken as the reference. In the following ultrasound images generated from ultrasound wave signals in the imaging system 100 that acquires ultrasound wave signals and photoacoustic signals will be described as being the reference.

In step S405, the external transmission information generating unit 127 selects image data to be displayed superimposed along with image data corresponding to the reference image information. The image data selected in step S405 does not necessarily have to be a layer image for superimposed display with the image data selected in step S404 as the base image. Image data for superimposed display is selected in S405 based on the image information set as the reference in step S404. In step S405, image information other than image information not selected in step S404 may be selected out of the correlated series of shot image information that has been acquired in step S403, or further narrowing down may be performed. In the narrowing down, image data is selected based on image quality and similarity of the image data, for example. The image data to be selected in step S405 is narrowed down by excluding part of image data from multiple image data with great similarity, taken at a close time. The object for superimposed display by the later-described processing is generated based on the combination of image information selected in step S404 and step S405.

In step S406, the external transmission information generating unit 127 determines whether or not the combination of shot image information selected in the processing up to step S405 is included in the superimposed image information 309. If included, that combination is not redundantly registered in the superimposed image identification information 304, and the flow advances to step S408. If not included, the flow advances to step S407.

In step S407, the external transmission information generating unit 127 adds the combination of shot image information selected in the processing up to step S405 in the superimposed image identification information 304 of the imaging procedure information 301.

In step S408, the external transmission information generating unit 127 determines whether or not determination has been completed regarding all of the series of image information that has been correlated, with regard whether or not to take as the object of superimposed display. IF completed, the flow advances to step S409. If not completed, the flow advances to step S404, and processing for this determination is continued.

In step S409, the external transmission information generating unit 127 executes superimposed image generating processing. Details of superimposed image generating processing will be described later with reference to FIG. 5.

In step S410, the external transmission information generating unit 127 determines whether or not determination has been completed regarding all shot image information included in the examination with regard whether or not to take as the object of superimposed display. If completed, the external transmission information generating unit 127 updates the information included in the imaging procedure information 301 and notifies the examination control unit 125 that processing of this determination has been completed, and the processing illustrated in FIG. 4 is ended. If not completed, the flow advances to step S403, and processing for this determination is continued.

Figure 5:
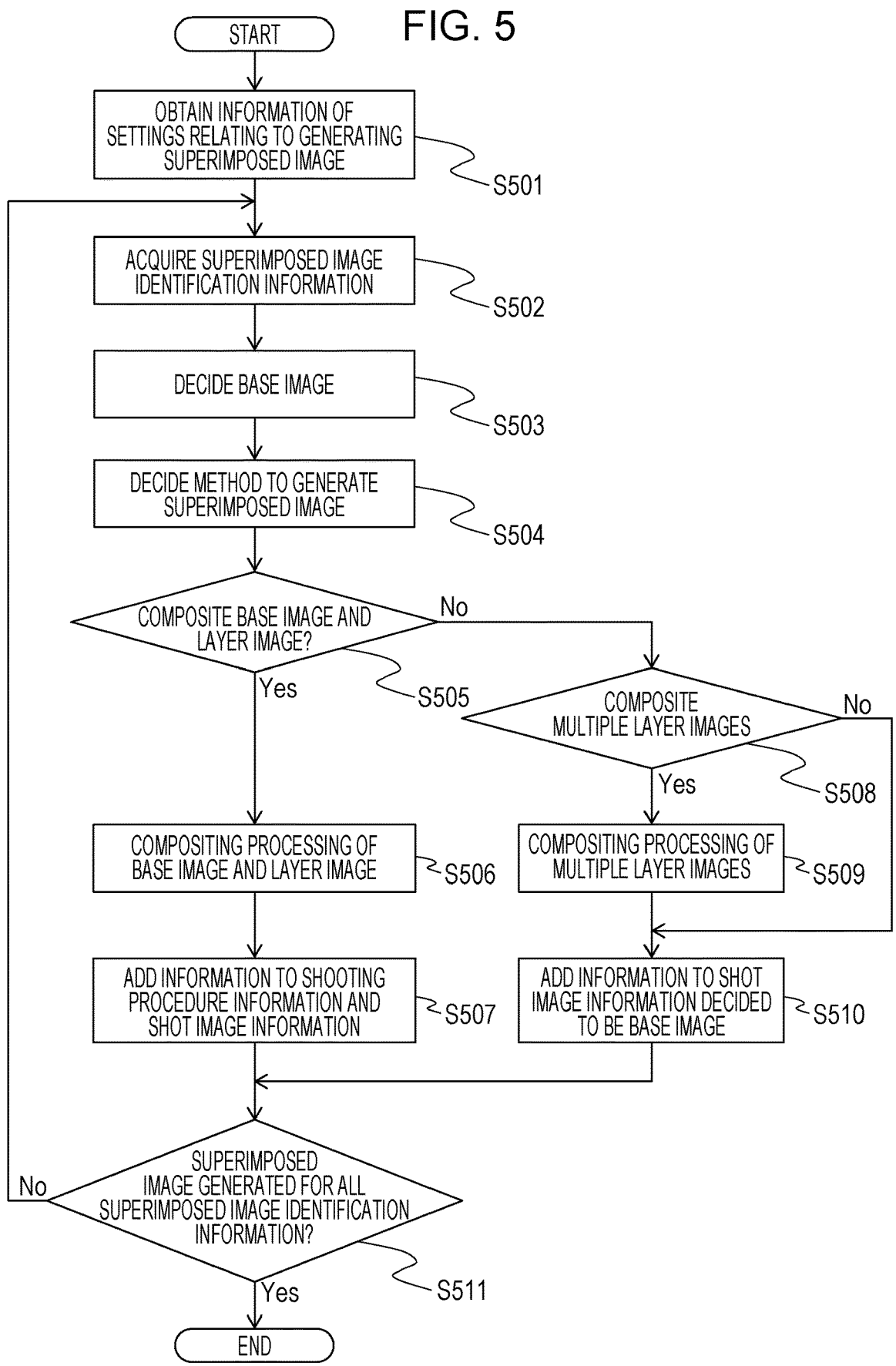
FIG. 5 is a flowchart illustrating an example of processing performed by the control device according to the embodiment of the present invention.

FIG. 5 is a flowchart illustrating an example of superimposed image generating processing performed in step S409 illustrated in FIG. 4.

In step S501, the external transmission information generating unit 127 acquires information relating to generating of a superimposed image from the settings saving unit 124. Information relating to generating of a superimposed image is obtained by various types of settings such as exemplified in FIG. 13, for example.

In step S502, the external transmission information generating unit 127 obtains one combination of image data to be the object of generating a superimposed image or a composite image, from the superimposed image identification information 304 registered in the imaging procedure information 301.

In step S503, the external transmission information generating unit 127 selects a base image for a superimposed image from the combination obtained in step S502.

In step S504, the external transmission information generating unit 127 decides a method for superimposing another image data on the base image selected in step S503 to generate a superimposed image. The external transmission information generating unit 127 decides the method and order of superimposing image data other than the image data selected in step S503 as the base image, out of the combination acquired in step S502, upon the base image. The external transmission information generating unit 127 then generates the superimposed image information 309.

Figure 13:
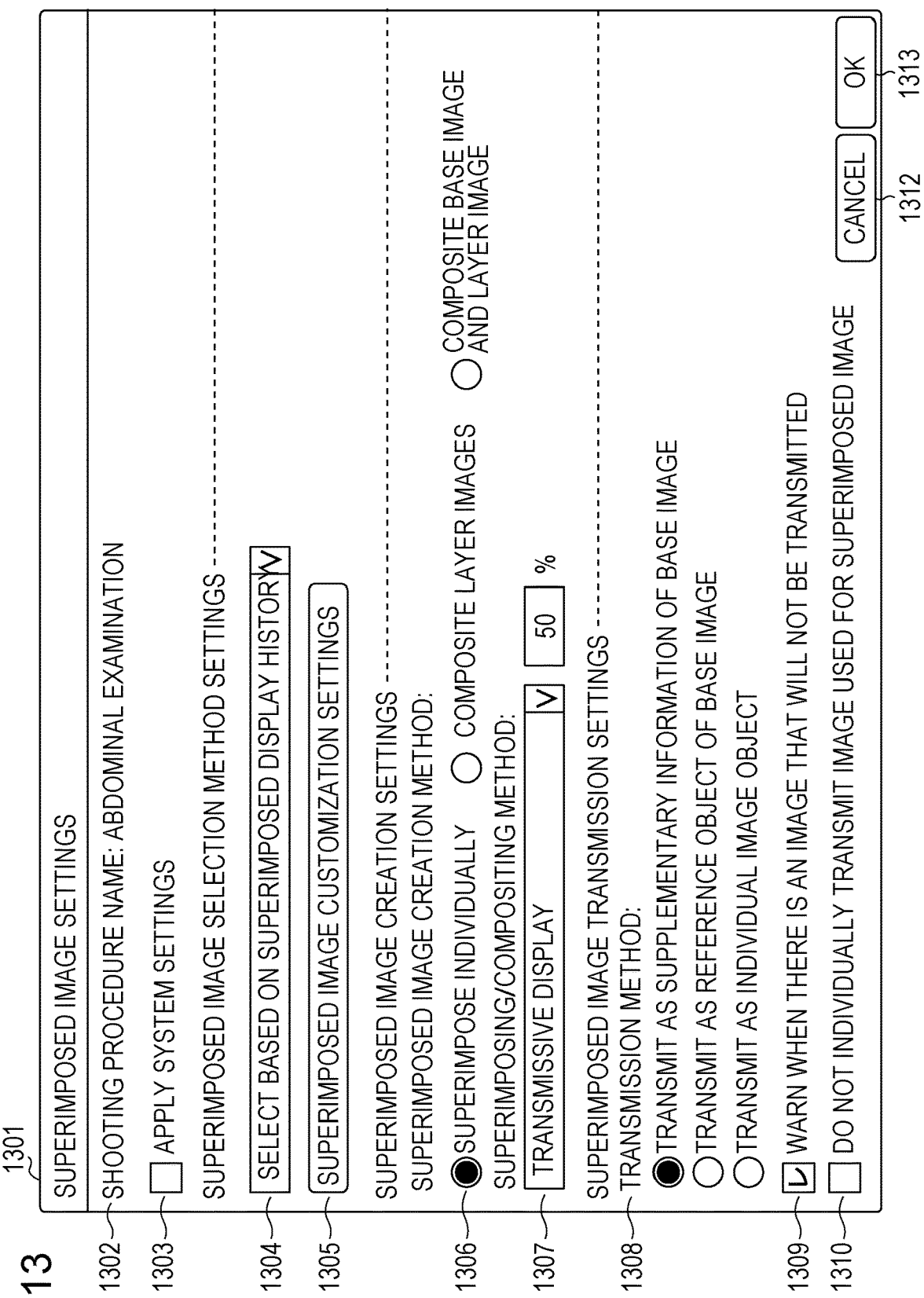
FIG. 13 is a diagram illustrating an example of a screen displayed on a display unit by the control device according to the embodiment of the present invention.

The method of selecting each of the base image and layer image, and superimposing in the processing in step S503 and step S504, is decided based on information in the settings 1306 illustrated in FIG. 13, for example. In the example illustrated in FIG. 13, the method of selecting the base image and layer image can be selected from "default selecting method", "customized selecting method", "select based on superimposed display history", and "select based on post-processing history", in settings 1304.

In a case where "default selecting method" is set, the external transmission information generating unit 127 selects the base image and layer image for the superimposed image based on the method stored in the control device 101 as the default value. In a case where "customized selecting method" is set, the external transmission information generating unit 127 obtains information of the corresponding customized settings from the settings saving unit 124. The external transmission information generating unit 127 then selects the base image and layer image for the superimposed image based on the information of the customized settings.

Examples of methods that can be set by "default selecting method" and "customized selecting method" includes a selecting the base image and layer image based on the image type information 308, for example. For example, in a case where image data and waveform data coexist in the imaging procedure information 301, settings can be made to generate a superimposed image only among image data. Also, image data of a particular type of image can be set to be taken as the base image. For example, a form image with detailed form information, like a B-mode image that is an example of an ultrasound image, may be set to be taken as a base image. In a case where information indicating whether a form image or a function image is included in the image type information 308, the base image and layer image may be selected based on this. A superimposed image can be efficiently interpreted by using a form image as the base image and a function image as the layer image. In another example, the combination of image data to generate the superimposed image can be selected based on information relating to positioning in the image type information 308. For example, in a case where a set of image data that has been positioned exists, a superimposed image can be generated among the positioned image data. In a case where no sets of image data that have been positioned exist in the plurality of shot image information, the external transmission information generating unit 127 may control the image processing unit 121 to perform positioning processing.

In a case where "select based on superimposed display history" is selected, the external transmission information generating unit 127 selects a base image and layer image for the superimposed image based on the superimposed display history information 310. For example, image data to serve as the reference, and image data for superimposed display, are selected based on input of user operations, and the form of superimposed display at the time of acquiring the image data to serve as the reference that has been selected by previous settings as described above. The image type of image data included in the superimposed image, superimposing method, and superimposing order, conform to the form of superimposed display at the time of acquiring the image data serving as the reference. In a case where no information is registered in the superimposed display history information 310, the input/output control unit 126 may display on the display unit 104 a screen annunciating to the user that no image that is the object exists. A screen for the user to select a base image and layer image from the series of shot image information that has been correlated, obtained in step S403, may be displayed.

In a case where "select based on post-processing history" is selected, the external transmission information generating unit 127 selects a base image and layer image for the superimposed image based on the post-processing history information 311. For example, with regard to image data to serve as a reference that has been selected by input of user operations or prior settings such as described above, for example, image data to be displayed superimposed with this image data to serve as a reference is selected based on the form of the superimposed display at the time of having performed post-processing. The image type of image data included in the superimposed image, superimposing method, and superimposing order, conform to the form of superimposed display when the base image was subjected to post-processing. Specifically, at the point of having performed image processing or processing to change the display state of this image data while making a preview display of this image data to serve as a reference, the external transmission information generating unit 127 selects the image data displayed superimposed together. For example, when displaying a B-mode image that is an example of an ultrasound image, and a region that could possibly be a tumor and the user should perform detailed observation has been found, there are cases where annotation is placed at this region. Alternatively here are cases where image processing is performed to view this region more clearly. If a photoacoustic image or the like is displayed superimposed on this B-mode image at the time of performing such post-processing, this photoacoustic image is judged to be useful as supplementary information for interpreting. On the other hand, if not superimposed display is performed, judgment is made that better interpreting can be performed without superimposing anything. Accordingly, a form that the user has judged to be suitable for interpreting can be reflected in the object for output to external devices. The external transmission information generating unit 127 references the image type information 308 of each of the shot image information 302 included in the superimposed image identification information 304. The external transmission information generating unit 127 selects image data of an image type that has detailed form information, out of the image data included in this combination, as the base image. An image type that has detailed form information is, for example, a B-mode image that is an example of an ultrasound image, as described earlier. In a case where multiple images that have detailed form information, such as a B-mode image and CT image or magnetic resonance imaging (MRI) image, for example, are included in the superimposed image identification information 304, the external transmission information generating unit 127 obtains the information of examinations of the same subject performed in the past from the examination implementation information saving unit 120. Situations are also conceivable where only image data having poor form information, such as some image types obtained based on photoacoustic waves, or single photon emission computed tomography (SPECT) images, exists in the superimposed image identification information 304. In this case, the external transmission information generating unit 127 obtains information of examinations performed on the same subject in the past from the examination implementation information saving unit 120. The external transmission information generating unit 127 searches the examination implementation information saving unit 120 for information of examinations performed by the same imaging procedure. In a case where information of examinations performed by the same imaging procedure is found, the external transmission information generating unit 127 selects a base image in the same way as the examination implemented in the past. In a case where no information of examinations performed by the same imaging procedure is found, the external transmission information generating unit 127 uses the oldest image data in the order of acquisition as the base image, for example.

In the example in FIG. 13, the superimposing method can be selected from "superimpose individually", "composite images for superimposing", and "composite base image and layer image" in the settings 1306.

In a case where the superimposing method is set to "composite base image and layer image", in step S505 the external transmission information generating unit 127 causes the image processing unit 121 to perform this compositing processing. The external transmission information generating unit 127 transmits the shot image information 302 corresponding to the base image and layer image, along with information indicating the superimposing method and superimposing order, to the image processing unit 121. In a case where the superimposing method is not "composite base image and layer image", the flow advances to step S508.

In step S506, the image processing unit 121 generates image data of the composited image where the base image and layer image have been superimposed and composited, based on the information received in step S505. The external transmission information generating unit 127 registers the image ID and image data in the composite image identification information 303, in order to identify the composited image.

In step S507, the external transmission information generating unit 127 updates the information of all shot image information 302 corresponding to the image data used in the composited image generated in step S506. The external transmission information generating unit 127 registers in the composite image identification information 303 the image ID for identifying the composited image generated in step S506.

In a case where the superimposing method is set to "composite layer images" in step S508, the external transmission information generating unit 127 causes the image processing unit 121 to perform this compositing processing. The external transmission information generating unit 127 transmits the shot image information 302 corresponding to base image and layer images, along with information indicating the superimposing method and superimposing order, to the image processing unit 121. In a case where the superimposing method is not "composite layer images", the flow advances to step S510.

In step S509, the image processing unit 121 generates a composited image where multiple layer images have been composited, based on the information received in step S508.

In step S510, the external transmission information generating unit 127 updates the information of the superimposed image information 309 in the shot image information 302 corresponding to the base image. The external transmission information generating unit 127 registers image IDs for identifying the image data used in the composited image for superimposing on the base image in step S509, in the superimposed image information 309. On the other hand, in a case where "superimpose individually" is selected as the superimposing method, or in a case where the count of layer images is one, a composited image is not generated. In this case, an image ID corresponding to image data to be superimposed is registered in the superimposed image information 309 of the shot image information 302 corresponding to the base image.

In step S511, the external transmission information generating unit 127 determines whether or not the processing up to step S510 has been completed for all image data that is the object of generating a superimposed image or composited image. Image data that is the object of generating a superimposed image or composited image is identified from the superimposed image identification information 304 registered in the imaging procedure information 301. In a case where this processing is not completed for all image data, the flow advances to step S502. If completed, the processing illustrated in FIG. 5 is ended.

The series of processing illustrated in FIG. 5 has been described as being an example of detailed processing of step S409 illustrated in FIG. 4, but this is not restrictive. For example, the base image for superimposed display in step S404 in FIG. 4 may be selected, and the layer image to superimpose on this base image layer may be selected in step S405 based on the settings illustrated in FIG. 13. The image data selected in step S404 may then be identified in step S503, and the image data selected in step S405 identified in step S504, thereby realizing the series of processing illustrated in FIG. 5.

Figure 6B:
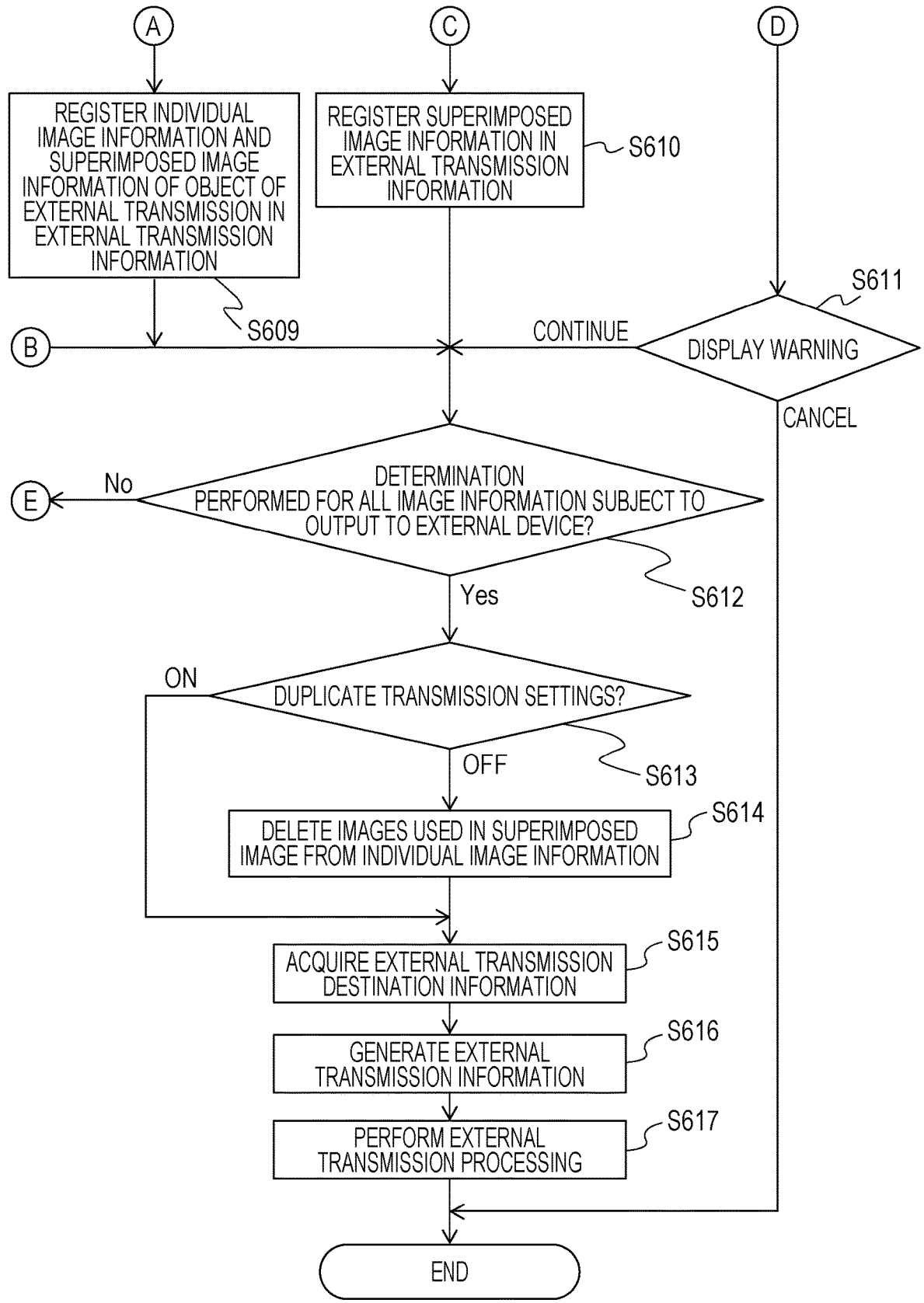

FIGS. 6a and 6B are flowcharts illustrating an example of processing for transmitting an object of displaying a superimposed image from the control device 101 to an external device.

In step S601, the examination control unit 125 accepts an instruction to output information including image data to an external device. Instruction of this input may be performed by input of user operations, or may be performed having been triggered by particular processing having been performed. The examination control unit 125 controls the external transmission information generating unit 127 to generate an object including the image data to be transmitted to the external device. The object of image data to be transmitted to the external device includes image data, and various types of information supplemented in accordance with the DICOM standard, for example. The object transmitted to the external device does not necessarily have to include image data. The examination control unit 125 transmits information such as patient information, examination information, and imaging procedure information 301, that is information necessary to generate the object, to the external transmission information generating unit 127.

In step S602, the external transmission information generating unit 127 acquires the shot image information 302 corresponding to the image data regarding which output to the external device has been instructed in step S601.

In step S603, the external transmission information generating unit 127 acquires a single image information from the shot image information 302 acquired in step S602.

In step S604, the external transmission information generating unit 127 obtains the failed shot information 306 included in the shot image information 302. In a case where the failed shot information 306 is set to ON, the flow advances to step S605, and in a case of being set to OFF, advances to step S607.

In step S605, the external transmission information generating unit 127 effects control so that the failed shot image of which the failed shot information 306 is ON, and a superimposed image and composited image including this failed shot image, are not output to the external device. Specifically, the external transmission information generating unit 127 references all image information groups correlated to this failed shot image. In a case where the image ID of this failed shot image is registered on the superimposed image information 309, the external transmission information generating unit 127 deletes the image ID of this failed shot image from the superimposed image information 309, composite image information 312, composite image identification information 303, and superimposed image identification information 304.

In step S606, the external transmission information generating unit 127 determines whether or not a storage device (omitted from illustration) for storing failed shot images is connected to the control device 101. An example of a storage device (omitted from illustration) for storing failed shot images is an image server. Generally, failed shot images are unsuitable for interpreting, and accordingly are not transmitted to the PACS 113. However, there are cases of using failed shot images for exchanging information among users or for educational proposes, so there are cases where this storage device is provided to manage failed shot images. In a case where the storage device (omitted from illustration) for storing failed shot images and the control device 101 are connected, the flow advances to step S609, and in a case of not being connected, advances to step S612.

In step S607, the external transmission information generating unit 127 acquires the external transmission permission/non-permission information 307 included in the shot image information 302. In a case where the external transmission permission/non-permission information 307 is set to ON, the flow advances to step S609, and in a case of being set to OFF, advances to step S608.

In step S609, the external transmission information generating unit 127 generates an image object 1102 based on the shot image information corresponding to the image data regarding which output to the external device has been instructed in step S601.

In step S608, the external transmission information generating unit 127 determines whether or not the shot image information 302 corresponding to the image data regarding which output to the external device has been instructed in step S601 is being used in any of a base image of superimposed display, layer image, or composited image. In a case of being used in any, the flow advances to step S610, and in a case of being used in none, advances to step S611.

In step S610, the external transmission information generating unit 127 records information of the superimposed image information 309 in the external transmission information 1101. The external transmission permission/non-permission information 307 is set to OFF in the shot image information 302 in step S610, so individual image data is not output to the external device, and can be output as a superimposed image or composite image.

Figure 10:
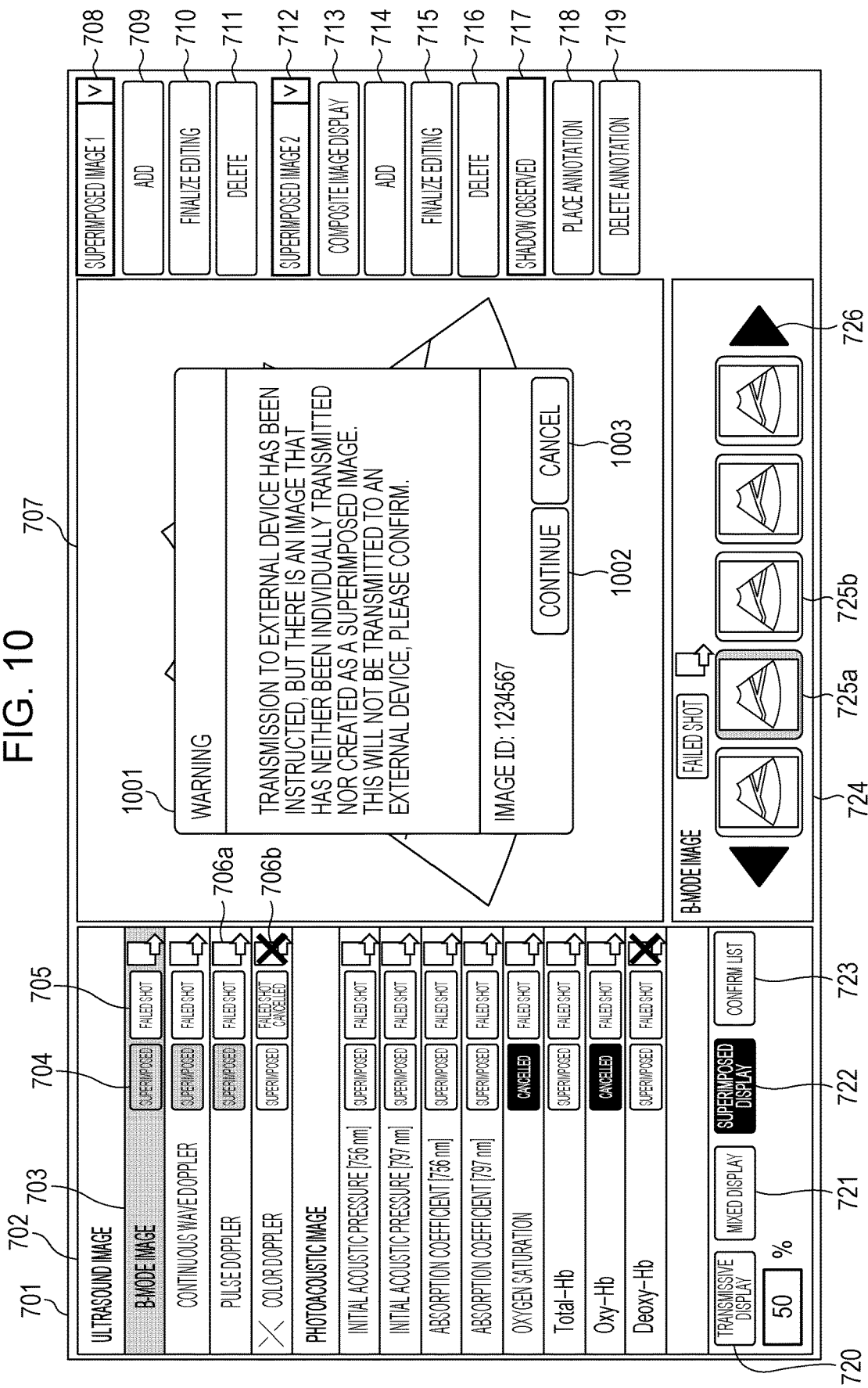
FIG. 10 is a diagram illustrating an example of a screen displayed on a display unit by the control device according to the embodiment of the present invention.

In step S611, the input/output control unit 126 displays a warning on the display unit 104. The transmission permission/non-permission information 307 is set to OFF in the shot image information 302 in step S611, and is not used in any of the base image of the superimposed image, layer image, or composite image, so the image data corresponding to this shot image information 302 is not output to the external device. Accordingly, the input/output control unit 126 makes a popup display of a warning dialog 1001 on the imaging screen 701 such as exemplified in FIG. 10, for example. A message for annunciating to the user that there is image data not transmitted to an external device, and the image ID of the image data that is not transmitted to the external device, are displayed in the warning dialog 1001. Further, a continuation instructing portion 1002 to instruct continuation of transmission processing to the external device, and a cancellation instruction portion 1003 to instruct cancelling of this transmission processing are displayed on the warning dialog 1001. When the continuation instruction portion 1002 is pressed, the warning dialog 1001 is closed, and the transmission processing relating to other image data is continued without changing the settings of the image which are settings of not being transmitted to an external device. When the cancellation instructing portion 1003 is pressed, the warning dialog 1001 is closed, and the transmission processing is canceled. In a case where settings 1309 illustrated in FIG. 13 are set to OFF, the input/output control unit 126 does not display the warning on the display unit 104.

In step S612, the external transmission information generating unit 127 determines whether or not the processing up to step S611 has been completed for all shot image information corresponding to the image data regarding which instruction has been given for output to the external device in step S601. In a case where this is not completed, the flow advances to step S603 and repeats the processing, and in a case of being completed, the flow advances to step S613.

In step S613, the external transmission information generating unit 127 acquires information relating to duplicate transmission settings, which are setting regarding whether or not to individually transmit image data used in a superimposed image or composite image, from the settings saving unit 124. The duplicate transmission settings are set at settings 1310 illustrated in FIG. 13, for example. In a case where the duplicate transmission settings are ON, the flow advances to step S615, and in a case of OFF, advances to step S614.

In step S614, the external transmission information generating unit 127 deletes, from shot image information registered in the external transmission information 1101, that corresponding to image data used in a superimposed image or composite image.

In step S615, the external transmission information generating unit 127 acquires information relating to the external device regarding which output has been instructed in step S601. Examples of information relating to the external device include information relating to DICOM-pursuant functions of the PACS 113 or viewer 114, and information of functions relating to superimposed display. Specific examples are information of reception and display of Information Object Definition (IOD) objects such as grayscale softcopy presentation state (GSPS) and color soft copy presentation state (CSPS) in DICOM, and information relating to functions of performing superimposed display of individually-received image data. The external transmission information generating unit 127 acquires information relating to the external device from the PACS 113 or viewer 114 via the network 110 at an optional timing.

Alternatively, when connection is made between the control device 101 and the PACS 113 or viewer 114, information relating to these external devices may be stored in the settings saving unit 124, and the external transmission information generating unit 127 may acquire this information from the settings saving unit 124.

In step S616, the external transmission information generating unit 127 generates the external transmission information 1101 for transmission to the external device, based on the information acquired in step S615. The external transmission information generating unit 127 generates the external transmission information 1101 based on the superimposed image identification information 304, composite image identification information 303, and superimposed image information 309 of each shot image information 302, of the imaging procedure information 301. The external transmission information generating unit 127 decides a generating method of the image object 1102 that is an object for displaying a superimposed image, based on settings relating to the transmission method set beforehand. The settings relating to this transmission method are set at settings 1308 illustrated in FIG. 13, for example.

The shot image information 302 individually transmitted, and the shot image information 302 selected as a base image of the superimposed image, are generated as individual image information 1103 of the image object 1102 in the external transmission information 1101, regardless of the contents of settings for the transmission method in the settings 1308. Also, the composite image identification information 303 is generated as composite image information 1104 of the image object 1102, regardless of the contents of settings for the transmission method in the settings 1308. The superimposed image information 309 is then generated based on the settings set for the transmission method in the settings 1308.

In a case where "transmit as supplementary information of base image" has been selected, the superimposed image information 309 is stored in the superimposed image information 1108 included in the individual image information 1103 of the corresponding base image. In a case where "transmit as reference object of base image" is selected, the superimposed image information 309 is stored as superimposing reference image information 1105 in the image object 1102, for each superimposed image data. The image ID of the base image corresponding to the supplemental information 1111 is input. In a case where "transmit as individual image object" is selected, the superimposed image information 309 is stored as individual image information 1103 in the image object 1102 for each image data.

Also, the image object 1102 of the external transmission information 1101 may be created conforming to a format defined in DICOM. In a case of being created conforming to a format defined in DICOM, shot image information 302 to be individually transmitted, shot image information 302 selected as a base image, and composite image identification information 303 are generated as a DICOM image file 1201 illustrated in FIG. 12, regardless of the transmission method settings. The superimposed image information 309 is then generated based on the transmission method settings.

In a case where "transmit as supplementary information of base image" has been selected, the superimposed image information 309 is stored in overlay image data 1206 included in the DICOM image file 1201 of the corresponding image (base image for superimposed display). In a case where "transmit as reference object of base image" has been selected, the superimposed image information 309 is generated as a GSPS object 1207 for each image data. A service object pair instance unique identifier (SOP Instance UID) 1204 of the corresponding base image is input to a reference SOP Instance UID 1208. In a case where "transmit as individual image object" has been selected, the superimposed image information 309 is created as a DICOM image file 1201 for each image data. Note that in the following, an example of a DICOM GSPS object will be used, but other objects may be used, such as CSPS objects or the like.

A case is conceivable where overlay image data 1206 included in the header information 1202 of the DICOM image file 1201 or GSPS object 1207 defined in DICOM has a different bit width for pixel values from an image data group included in the imaging procedure information 301. In this case, the pixel values of the superimposed image information 309 included in the imaging procedure information 301 are converted into values storable in the overlay image data 1206, and then input.

Further, the external transmission information generating unit 127 may control the generating method in accordance with information relating to the external device acquired in step S615. For example, in a case where the PACS 113 or viewer 114 has functions of superimposed display of image data individually transmitted, a generating method the same as the "transmit as individual image object" settings is used. Accordingly, the user who has displayed this image object using the viewer 114 can display as a superimposed image for example, and also can display individual images. Also, in a case of the external device having functions of receiving and displaying a GSPS object, a generating method the same as the "transmit as reference object of base image" settings is used. In a case where the external device has neither of these functions, a generating method the same as the "transmit as supplementary information of base image" settings is used.

In step S617, the transmission/reception control unit 128 transmits the object generated in step S616 to the external device. The external transmission information generating unit 127 transmits the generated external transmission information 1101 to the examination control unit 125. The examination control unit 125 transmits the external transmission information 1101 to the external device via the transmission/reception control unit 128.

Figure 7:
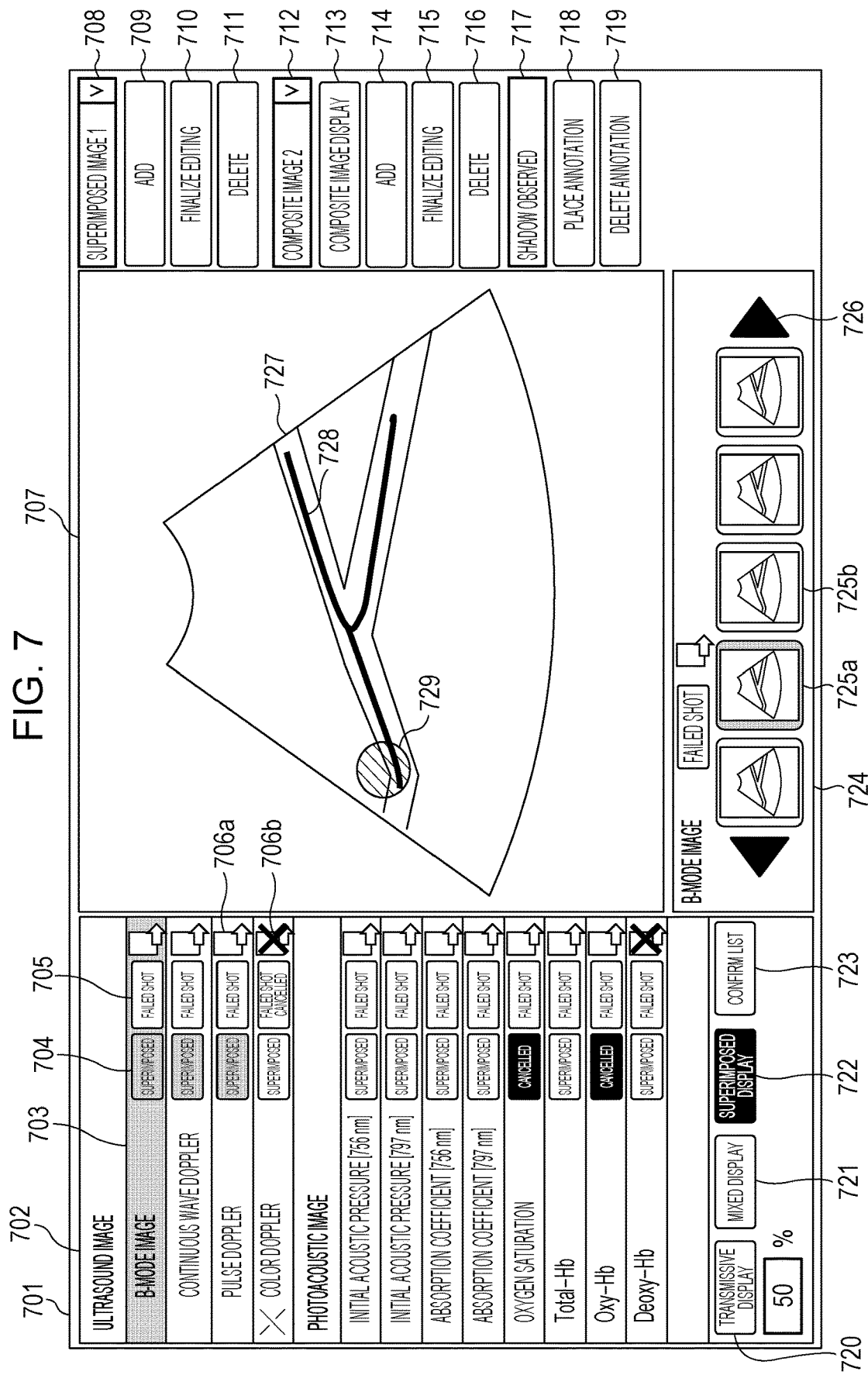
FIG. 7 is a diagram illustrating an example of a screen displayed on a display unit by the control device according to the embodiment of the present invention.

FIG. 7 is a diagram illustrating an example of a imaging screen 701 displayed on the display unit 104 by the control device 101. The imaging screen 701 includes a related image list 702, a related image item 703, a superimposing instruction portion 704, a failed-shot instructing portion 705, a transmission instructing portion 706, an image display portion 707, a superimposed image switching portion 708, a superimposed image adding portion 709, a superimposed image finalizing portion 710, a superimposed image deleting portion 711, a composite image switching portion 712, a composite image display instructing portion 713, a composite image adding portion 714, a composite image finalizing portion 715, a composite image deleting portion 716, an annotation input portion 717, an annotation placement portion 718, an annotation deleting portion 719, a transmissive display instruction portion 720, a mixed display instruction portion 721, a superimposed display instruction portion 722, a list confirmation portion 723, a thumbnail image display portion 724, thumbnail images 725, and page switching instruction portions 726.

The related image list 702 is a list of all images correlated with a thumbnail images 725a that is in a selected state in the thumbnail image display portion 724. In a case where all information of the related image list 702 cannot be displayed on the display unit 104 as a list, the display of the related image list 702 is switched by scrolling. The related image item 703 is displayed in each row of the related image list 702. Although the related image list 702 is shown as being distinguished according to imaging types in the example in FIG. 7, images taken in a correlated manner in the examination and corresponding related image items 703 may be displayed included in a single list.

The related image item 703 is a list item corresponding to image data in a one on one manner. A text string representing the name of the image data, the superimposing instruction portion 704, the failed-shot instructing portion 705, and the transmission instructing portion 706 are displayed within the related image item 703. A thumbnail image of the corresponding image data may be displayed in the related image item 703 instead of the text string representing the name of the image data, or both the text string and thumbnail image may be displayed together. The user can perform input operations regarding the related image item 703, and can select the related image item 703. Image data corresponding to the selected related image item 703 is displayed on the image display portion 707. The related image item 703 corresponding to the B-mode image of ultrasound images is selected in the example illustrated in FIG. 7, and a B-mode image 727 is displayed in the image display portion 707.

The superimposing instruction portion 704 is a button that instructs for the image corresponding to the related image item 703 to be superimposed on the image preview-displayed in the image display portion 707. When the superimposing instruction portion 704 is set to ON, the corresponding image is displayed superimposed as a layer image on the preview-displayed image. When the superimposing instruction portion 704 is set to OFF, the image that was displayed superimposed on the preview-displayed image is hidden from display. In the example in FIG. 7, an oxygen saturation image 728 and an oxyhemoglobin amount 729 are displayed superimposed on the preview-displayed B-mode image 727. Note that the superimposing instruction portion 704 will be set to OFF for related image items 703 regarding which superimposed display would be meaningless. For example, A-mode waveform data and M-mode temporal axis data generated from ultrasound wave signals have the superimposed display regarding B-mode images set to OFF.

The failed-shot instructing portion 705 is a button for performing failed-shot processing regarding image data corresponding to the related image item 703. When failed-shot processing is executed, the failed shot information 306 corresponding to this image data is switched to ON. A failed-shot mark indicating that this is a failed-shot image is also displayed on the related image item 703. When the failed-shot execution is cancelled, the failed shot information 306 is switched to OFF. The failed-shot mark in the related image item 703 also is hidden from display.

The transmission instructing portion 706 is a button for individually instructing whether or not to transmit the image data corresponding to the related image item 703 to an external device. When the transmission instructing portion 706 is switched to ON, the transmission permission/non-permission information 307 corresponding to this image data is switched to ON. The transmission instructing portion 706 is displayed in different forms according to the ON and OFF settings. In the example in FIG. 7, in the case of ON, display is made in the form of a transmission instructing portion 706a, and in the case of OFF, display is made in the form of a transmission instructing portion 706b.

Thus, failed-shot processing and transmission to external devices can be set for each related image item 703, i.e., for each image data, at the control device 101. The failed-shot instructing portion 705 and transmission instructing portion 706 can also be set separately, so the control device 101 can distinguish whether the reason of not being transmitted to an external device is due to a failed shot or not. Note that in the example in FIG. 7, failed-shot instructing portions 705 and transmission instructing portions 706 are displayed regarding all related image items 703 in the related image list 702, and are settable. This example is not restrictive, however, and an arrangement may be made where the failed-shot instructing portion 705 and transmission instructing portion 706 are displayed and selectable only for the related image item 703 corresponding to image data displayed in the image display portion 707.

The image display portion 707 is a region for displaying medical images obtained by the imaging system 100. Images displayed in the image display portion 707 may be any type of image, such as still images, moving images, waveform data, and so forth. An image is preview-displayed in the image display portion 707 in real-time while imaging a moving image. Image data corresponding to the related image item 703 selected from the related image list 702 is preview-displayed on the image display portion 707.

The superimposed image switching portion 708 is a region for switching superimposed display registered in the superimposed image information 309 corresponding to the image data preview-displayed in the image display portion 707. The superimposed image switching portion 708 displays options of "no display", and selection from superimposed displays registered in the superimposed image information 309. Image data selected at the superimposed image switching portion 708 is displayed as a layer image for the image data preview-displayed in the image display portion 707. In a case where "no display" is selected, no image data is superimposed.

The superimposed image adding portion 709 is a button for adding the state superimposed-displayed on the image display portion 707, to the superimposed image information 309 of image data corresponding to the related image item 703 selected so as to make the preview display in the image display portion 707. Superimposed image information 309 reflecting the form of the superimposed display in the image display portion 707 at the point that the superimposed image adding portion 709 is pressed is generated. This form of superimposed display is a form regarding image data superimposed as layer images, and the superimposing order thereof. If there has been no registration made reflecting the same superimposed display form of the superimposed image information 309 generated, in the superimposed image information 309 of image data corresponding to the related image item 703 selected for the preview display in the image display portion 707, this is newly added. When information of the superimposed image information 309 is updated, the options of the superimposed image switching portion 708 also are updated.

The superimposed image finalizing portion 710 is a button for confirming the superimposed display form, and instructing updating of the contents of the superimposed image information 309. The superimposed display form selected at the superimposed image switching portion 708 is updated to contents reflecting the superimposed display form at the point that the superimposed image finalizing portion 710 was pressed. In the example illustrated in FIG. 7, the superimposed display form registered as "superimposed image 1" is updated to the form at the point at which the superimposed image finalizing portion 710 is pressed. Accordingly, the superimposed image information 309 is finalized. In a case where "no display" is selected from the superimposed image switching portion 708, the superimposed image finalizing portion 710 is disabled.

The superimposed image deleting portion 711 is a button for instruction deletion of the contents of the superimposed image information 309 that have been registered. When the superimposed image deleting portion 711 is pressed, information corresponding to the selected superimposed display form is deleted from the superimposed image information 309, and deleted from the options in the superimposed image switching portion 708. Further, superimposed display in the image display portion 707 is cancelled. In a case where "no display" has been selected from the superimposed image switching portion 708, the superimposed image deleting portion 711 is disabled.

The composite image switching portion 712 is a region for switching display of composite image data corresponding to the composite image identification information 303 registered in the imaging procedure information 301. The composite image switching portion 712 displays options of "no display", and selection from composite images registered in the imaging procedure information 301.

The composite image instructing portion 713 is a button for instructing display of the composite image selected at the composite image switching portion 712 in the image display portion 707. At the point that the composite image instructing portion 713 is pressed, the composite image selected at the composite image switching portion 712 is displayed in the image display portion 707. In a case where "no display" is selected at the composite image switching portion 712, no composite image is displayed in the image display portion 707. At the point that the composite image display instructing portion 713 is pressed, image data displayed at the image display portion 707 is hidden from display.

The composite image adding portion 714 is a button for instructing generating of a composite image where a plurality of image data superimposed-displayed in the image display portion 707 has been composited, and addition to the composite image identification information 303 in the imaging procedure information 301. If composite image identification information 303 of the same form as that superimposed-displayed in the image display portion 707 has not been registered in the imaging procedure information 301, this is newly added. When the information of the composite image identification information 303 is updated, the options in the composite image switching portion 712 are also updated.

The composite image finalizing portion 715 is a button for instruction to finalize the superimposed display form of the composite image, and update the contents of the composite image identification information 303. The superimposed display form of the composite image selected at the composite image switching portion 712 is changed to the contents reflecting the superimposed display form at the point that the composite image finalizing portion 715 was pressed. In the example illustrated in FIG. 7, the superimposed display form registered as "composite image 2" is updated to the superimposed display form at the point that the composite image finalizing portion 715 was pressed. Thus, the composite image identification information 303 is updated. In a case where "no display" has been selected at the composite image switching portion 712, the composite image finalizing portion 715 is disabled.

The composite image deleting portion 716 is a button for instructing deletion of the registered contents of the composite image identification information 303. When the composite image deleting portion 716 is pressed, the information corresponding to the selected composite image is deleted from the composite image identification information 303, and deleted from the options in the composite image switching portion 712. Display of the composite image in the image display portion 707 is cancelled. In a case where "no display" is selected at the composite image switching portion 712, the composite image deleting portion 716 is disabled.

The annotation unit portion 717 is a region for inputting a text string for annotation to be placed in the image display portion 707. The annotation placement portion 718 is a button for instructing placement of the text string input to the annotation unit portion 717 on the image data displayed in the image display portion 707. The text string input to the annotation input portion 717 at the point that the annotation placement portion 718 is pressed becomes annotation data, and is placed in the image display portion 707. The annotation deleting portion 719 is a button for instructing deletion of an annotation placed in the image display portion 707. Upon pressing the annotation deleting portion 719 in a state where one of the annotations placed in the image display portion 707 is selected, the selected annotation is deleted.

The transmissive display instruction portion 720 is a region for changing the transmissivity of the layer image displayed superimposed in the image display portion 707. The mixed display instruction portion 721 is a button for instructing switching of the superimposed display in the image display portion 707 to mixed display. This mixed display is a display method where pixel values of overlaid pixels are mixed and displayed in the superimposed display of a plurality of image data. The mixed display corresponds to an example of "display overlaid portions using different color" in illustrated in FIG. 8, for example. The superimposed display instruction portion 722 is a button for instructing to specify the superimposing order of layer images for superimposed display in the image display portion 707, and switch to superimposed display according to the specified order. Note that one is selected from the three of the transmissive display instruction portion 720, mixed display instruction portion 721, and superimposed display instruction portion 722, and the superimposed display method in the image display portion 707 switches in conjunction with switching of which of these is specified.

The list confirmation portion 723 is a button for instructing displaying a list of external transmission information 1101 on the display unit 104 at the point of having been pressed. When the list confirmation portion 723 is pressed, a list screen 901 pops up on the imaging screen 701.

The thumbnail image display portion 724 is a region displaying thumbnail images corresponding to image data selected as references from the plurality of image data correlated in the examination. The thumbnail image display portion 724 includes the failed-shot instructing portion 705, transmission instructing portion 706, thumbnail images 725, and page switching instruction portions 726. The example in FIG. 7 illustrates display of thumbnail images of a series of B-mode images that are an example of ultrasound images, in the time sequence of acquisition. For example, there are conceivably cases where, while taking ultrasound images, photoacoustic signals are acquired at an optional timing to obtain photoacoustic signals, and photoacoustic images are acquired. It is further conceivable that the acquired ultrasound images and photoacoustic images will be compared and observed by superimposed display, for example. As described above, the control device 101 selects an ultrasound image as a reference image, for example. Accordingly, the ultrasound image selected as a reference is displayed in the thumbnail image display portion 724, and an image group correlated with the selected ultrasound image is displayed in the related image list 702. Note that the image type selected as a reference is not restricted to ultrasound images, and can be set and selected optionally, as described above.

For each bunch of image data acquired in one imaging procedure, for example, a thumbnail image 725 corresponding to each image data is displayed at the thumbnail image display portion 724. In a case where a moving image is acquired, a thumbnail image 725 corresponding to a representative frame image out of the multiple frames included in the moving image is displayed. Thumbnail images 725 corresponding to the sequentially-acquired image data are added to the thumbnail image display portion 724 in the imaging screen 701, each time image data is acquired, until the examination ends.

In response to the input of operation regarding a thumbnail image 725 displayed in the thumbnail image display portion 724, image data to be preview-displayed in the image display portion 707 is selected. The selected thumbnail image 725 goes to a preview-selected state (725*a*), and thumbnail images 725 that are not selected are in a non-preview-selected state (725*b*). Also, in conjunction with the thumbnail image 725 preview-displayed in the image display portion 707 being switched, the display of the failed-shot instructing portion 705 and transmission instructing portion 706 included in the thumbnail image display portion 724, and the related image item 703 displayed in the related image list 702, are updated. The failed-shot instructing portion 705 and transmission instructing portion 706 included in the thumbnail image display portion 724 indicate the failed-shot settings and transmission permission/non-permission settings regarding the thumbnail image 725*a* in the preview-selected state. In a case where all thumbnail images 725 cannot be displayed in the thumbnail image display portion 724, the page switching instruction portions 726 displayed are enabled. Pressing the page switching instruction portions 726 at the left and right of the thumbnail image 725 group switches the list of thumbnail images 725 displayed in the thumbnail image display portion 724.

FIGS. 8A through 8H are diagrams illustrating an example of superimposed displays set by the control device 101 and applied. The superimposing method of data for superimposed display using a plurality of image data, or composited image data, is switched by settings thereof. This superimposing method is selected from "transmissive display", "display overlaid portions using different color", "superimposed display according to order", "masked display" and "difference display", for example. Note that it is sufficient for the superimposing method to be stipulated for image processing using a plurality of image data, and is not restricted to the above options. An example of a case of using two image data of FIGS. 8A and 8B will be described below.

Figure 8A:
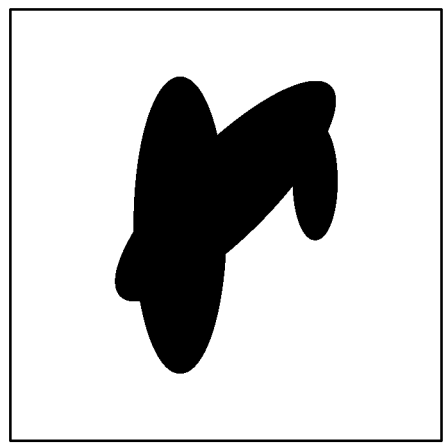
FIG. 8A is a diagram illustrating an example of a display form of a medical image by the control device according to the embodiment of the present invention.
Figure 8B:
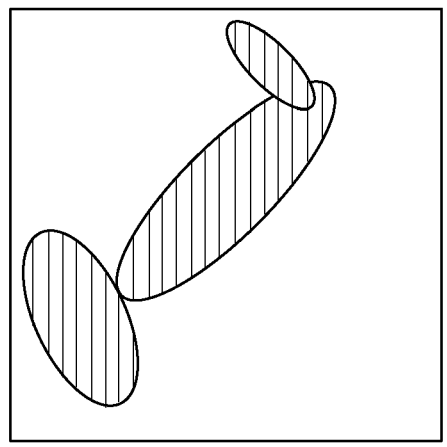
FIG. 8B is a diagram illustrating an example of a display form of a medical image by the control device according to the embodiment of the present invention.
Figure 8C:
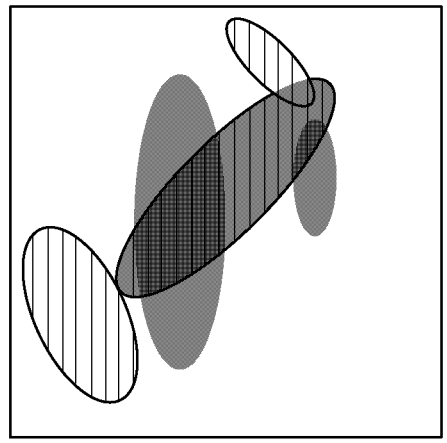
FIG. 8C is a diagram illustrating an example of a display form of a medical image by the control device according to the embodiment of the present invention.

FIG. 8C is an example of display in a case where the superimposing method is set to "transmissive display". The user can set the transmissivity of the layer image. At least one of the two image data is displayed at this set transmissivity.

Figure 8D:
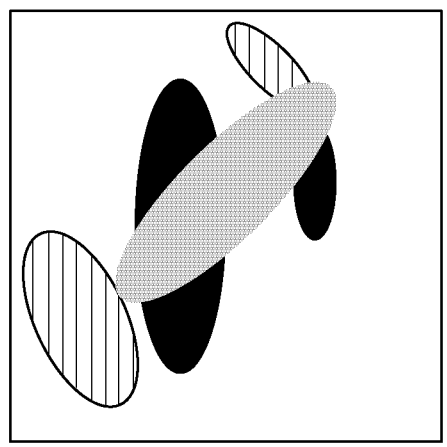
FIG. 8D is a diagram illustrating an example of a display form of a medical image by the control device according to the embodiment of the present invention.

FIG. 8D is an example of display in a case where the superimposing method is set to "display overlaid portions using different color". This is a display by a different color from that in a case where at least one of the two image data is displayed independently. Accordingly, the user can more readily visually recognize overlaid regions when superimposing two image data. For example, pixel values are decided for pixel values in the two image data having the same coordinates, and a superimposed image is displayed with a color where the display colors of each have been mixed. Where a pixel value is set for only one image data, and there are coordinates in the other image data where no pixel values exists or pixel values are 0, display may be made using the pixel values of the former image data, i.e., display using the original color of the former image data.

Figure 8E:
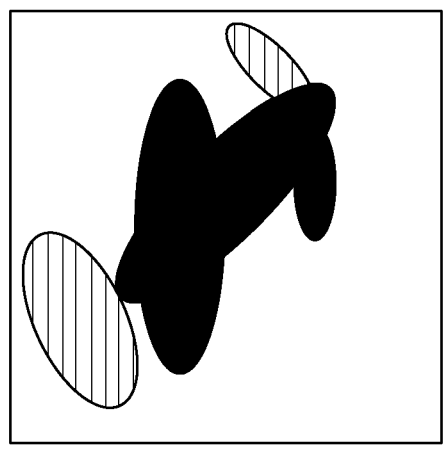
FIG. 8E is a diagram illustrating an example of a display form of a medical image by the control device according to the embodiment of the present invention.
Figure 8F:
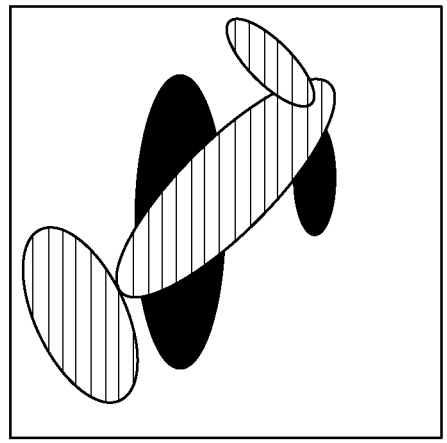
FIG. 8F is a diagram illustrating an example of a display form of a medical image by the control device according to the embodiment of the present invention.

FIGS. 8E and 8F are examples of a case of displaying with the superimposing method set to "superimposed display according to order". The user can set the superimposing order of layer images. FIG. 8E is a case where the user has set the image data in FIG. 8A as the layer image, and FIG. 8F is a case where the user has set the image data in FIG. 8B as the layer image.

Figure 8G:
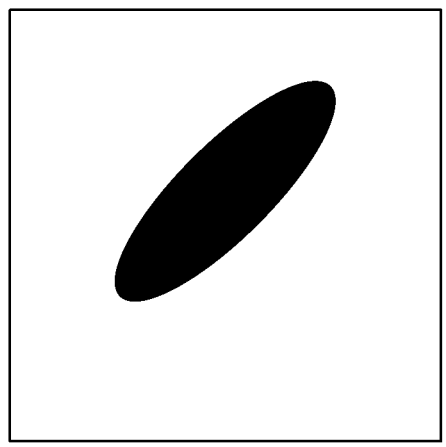
FIG. 8G is a diagram illustrating an example of a display form of a medical image by the control device according to the embodiment of the present invention.

FIG. 8G is an example of a display where the superimposing method has been set to "masked display". In the masked display, only coordinates where pixel values are overlaid among the base image and superimposed multiple layer images are displayed. Only pixel values for the base image are displayed for coordinates where pixel values exist in the layer image, and coordinates where there are no pixel values in the layer image are masked.

Figure 8H:
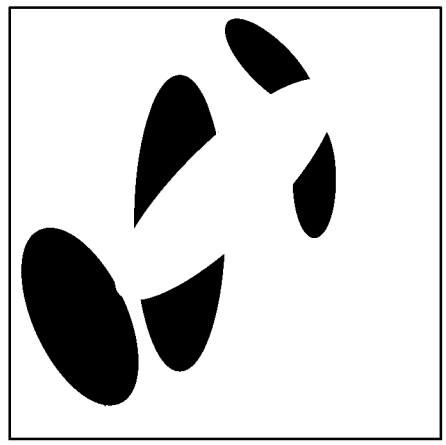
FIG. 8H is a diagram illustrating an example of a display form of a medical image by the control device according to the embodiment of the present invention.

FIG. 8H is an example of display in a case where the superimposing method is set to "difference display". In the difference display, coordinates where pixel values exist only in one of the base image and the superimposed layer images are displayed. Coordinates where pixel values exist in both base image and layer images are masked. Coordinates where pixel values exist in only one are displayed in the same way as the superimposing method "superimposed display according to order".

Thus, enabling switching among multiple superimposed display methods to display allows superimposed display corresponding to various interpreting usage cases to be easily performed.

FIG. 9 is a diagram illustrating an example of a screen for displaying external transmission information 1101 including objects for superimposed display to be transmitted to an external device, as a list. The list screen 901 is a screen where external transmission information 1101 can be confirmed in a list, for each imaging procedure in the examination being performed. The list screen 901 includes a list display switching portion 902, a imaging procedure name 903, a list display portion 904, and an end instruction portion 905.

The list display switching portion 902 is a region for switching between content to display as a list in the list display portion 904. In the example illustrated in FIG. 9, the content to be displayed in a list can be switched between "superimposed image" and "composite image". In a case where all external transmission information 1101 to be displayed cannot be displayed in the list display portion 904, a button for switching the groups of information displayed in the list display portion 904 will be displayed.

The imaging procedure name 903 is a region where the name of the imaging procedure relating to the image data displayed in the list display portion 904 is displayed.

The list display portion 904 is a region for displaying a list of external transmission information 1101. The external transmission information 1101 at the point that input of operation has been made at the list confirmation portion 723 illustrated in FIG. 7 and the list screen 901 is displayed, is displayed in the list display portion 904. In a case where "superimposed image" is selected as content to display a list of, the base image and layer images to be superimposed on this base image, are displayed in the list display portion 904. Image data to be individually transmitted is also displayed in the column of base images in the list display portion 904. One layer image is displayed in one cell in the list display portion 904. A state where the layer image has been superimposed on the base image following the superimposing method set beforehand is displayed in one cell. On the other hand, in a case where "composite image" is selected as the content to be displayed as a list, composited images where base images and layer images have been composited following the compositing method decided beforehand, are displaced in the list display portion 904. Although thumbnail images are displayed in the example illustrated in FIG. 9, this may be expressed by any form as long as the image type and superimposing method can be comprehended.

The end instruction portion 905 is a button for ending the list display of external transmission information 1101. When the end instruction portion 905 is pressed, the list screen 901 is closed.

Figure 11:
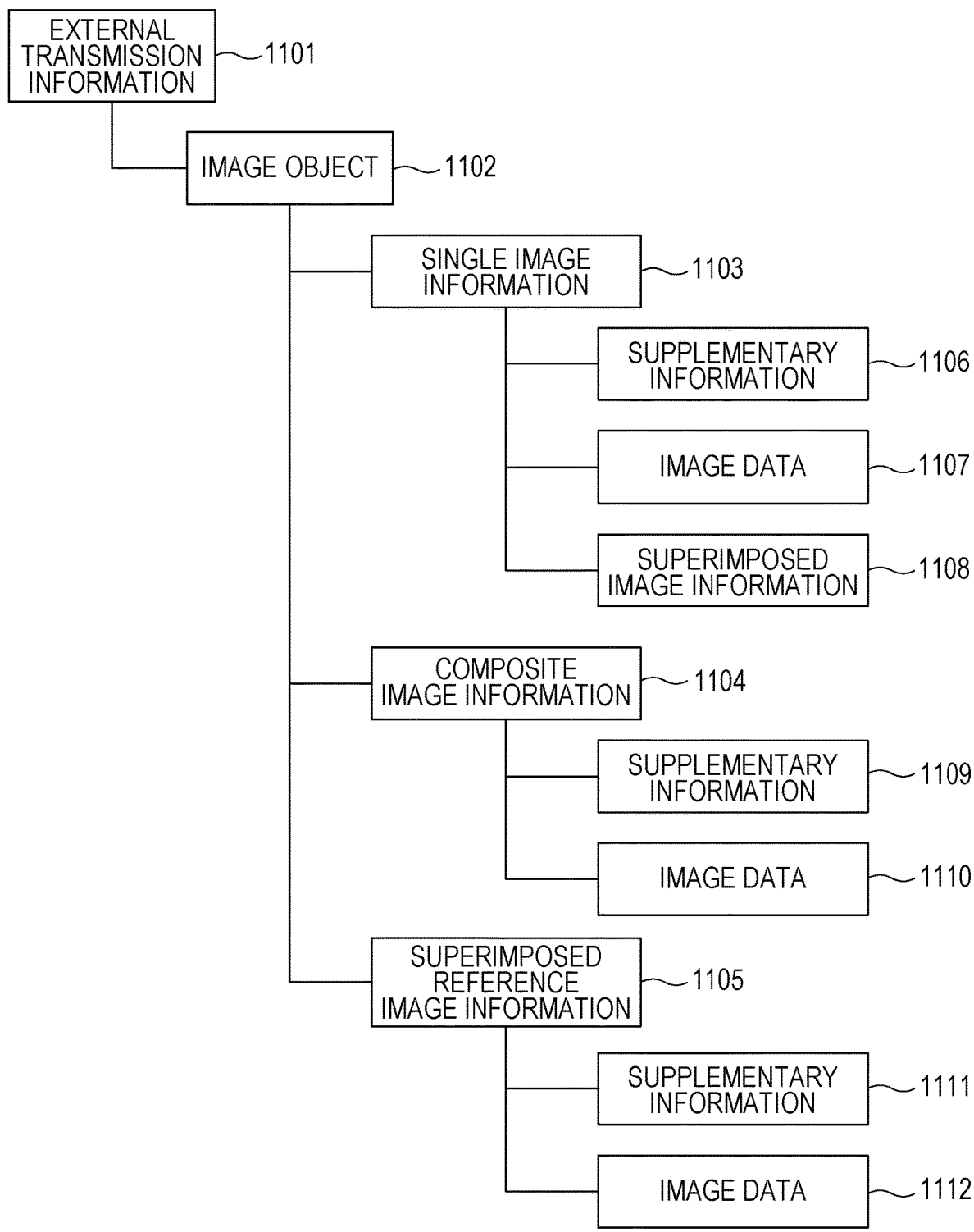
FIG. 11 is a diagram illustrating an example of information generated by the control device according to the embodiment of the present invention.

FIG. 11 is a diagram illustrating an example of the detailed structure of the external transmission information 1101 including objects transmitted to external devices. The external transmission information 1101 is information for transmitting image data acquired in examinations performed by the imaging system 100, image data for superimposed display that are generated from imaged image data, and image objects 1102 including composite images, together to external devices. Note however, that the control device 101 does not have to transmit all image objects 1102 at once, and may transmit over several times.

The image object 1102 includes at least one image information. The image information included in the image object 1102 is, for example, individual image information 1103, composite image information 1104, or superimposing reference image information 1105. A plurality of any of these image information may be included in the image object 1102, and if the relevant corresponding image data is not transmitted, the corresponding image information does not have to be included.

The individual image information 1103 includes image data imaged by the imaging system 100, and related information. The individual image information 1103 includes, for example, supplementary information 1106 and image data 1107. The supplementary information 1106 includes patient information, examination information, image ID, and like information. The supplementary information 1106 may include any data that identifies image data included in the image data 1107 and superimposed image information 1108. The supplementary information 1106 is recorded as header information of the image data 1107, for example. The supplementary information 1106 may be in any form, as long as a format that can be read by the PACS 113 or viewer 114. A plurality of superimposed image information 1108 may be included in the individual image information 1103. In a case where a plurality of superimposed image information 1108 is included, the individual image information 1103 includes, in the supplementary information 1106 for example, information whereby the superimposing order of each image data included in the superimposed image information 1108 can be identified. The individual image information 1103 correlates the superimposed image information 1108 including image data of layer images to be superimposed on image data 1107 serving as the base image. The individual image information 1103 is an example of an object that can be displayed superimposed at the external device.

The composite image information 1104 includes image data of composite images obtained by compositing a plurality of image data and related information. The composite image information 1104 includes, for example, supplementary information 1109 and image data 1110. The supplementary information 1109 includes information such as patient information, examination information, and image ID. The supplementary information 1109 may include any data that identifies the image data 1110. The supplementary information 1106 is recorded as the header information of the image data 1110, for example. The supplementary information 1109 may be in any form, as long as a format that can be read by the PACS 113 or viewer 114. The supplementary information 1109 further includes image IDs of individual image information 1103 corresponding to image data used to generate the composite image, and information indicating the compositing method. The image data 1110 is image data of this composite image.

The superimposing reference image information 1105 includes information for referencing the base image, and image data of layer images. The superimposing reference image information 1105 includes, for example, supplementary information 1111 and image data 1112. The supplementary information 1111 includes information such as patient information, examination information, and image ID. The supplementary information 1111 may include any data that identifies the image data 1112. The supplementary information 1111 is recorded as header information of the image data 1112, for example. The supplementary information 1111 may be in any form, as long as a format that can be read by the PACS 113 or viewer 114. The supplementary information 1111 also includes the superimposing method for superimposed display, and information of the image ID of the individual image information 1103 corresponding to the base image. The image data 1112 is image data of layer images. A plurality of superimposing reference image information 1105 may reference this individual image information 1103 as a base image. In this case, information by which the superimposing order of the multiple layer images can be identified is included in at least one of the supplementary information 1111 of the superimposing reference image information 1105, or the supplementary information 1106 of the individual image information 1103 of the base image. The superimposing reference image information 1105 correlates the layer images to be superimposed as to the image data referenced as the base image. The superimposing reference image information 1105 is an example of an object where superimposed display can be performed at an external device.

Figure 12A:
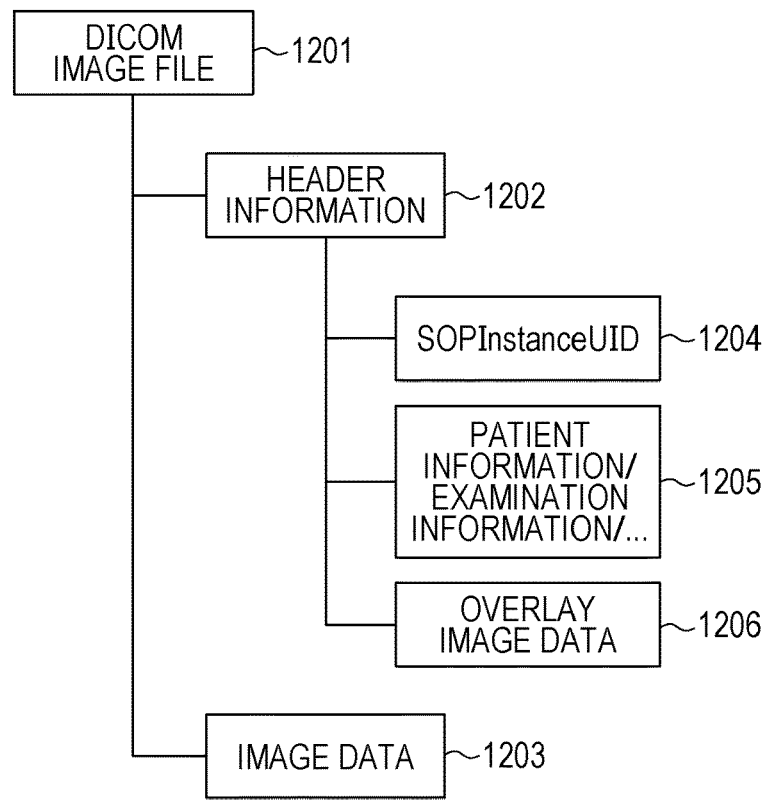
FIG. 12A is a diagram illustrating an example of information generated by the control device according to the embodiment of the present invention.
Figure 12B:
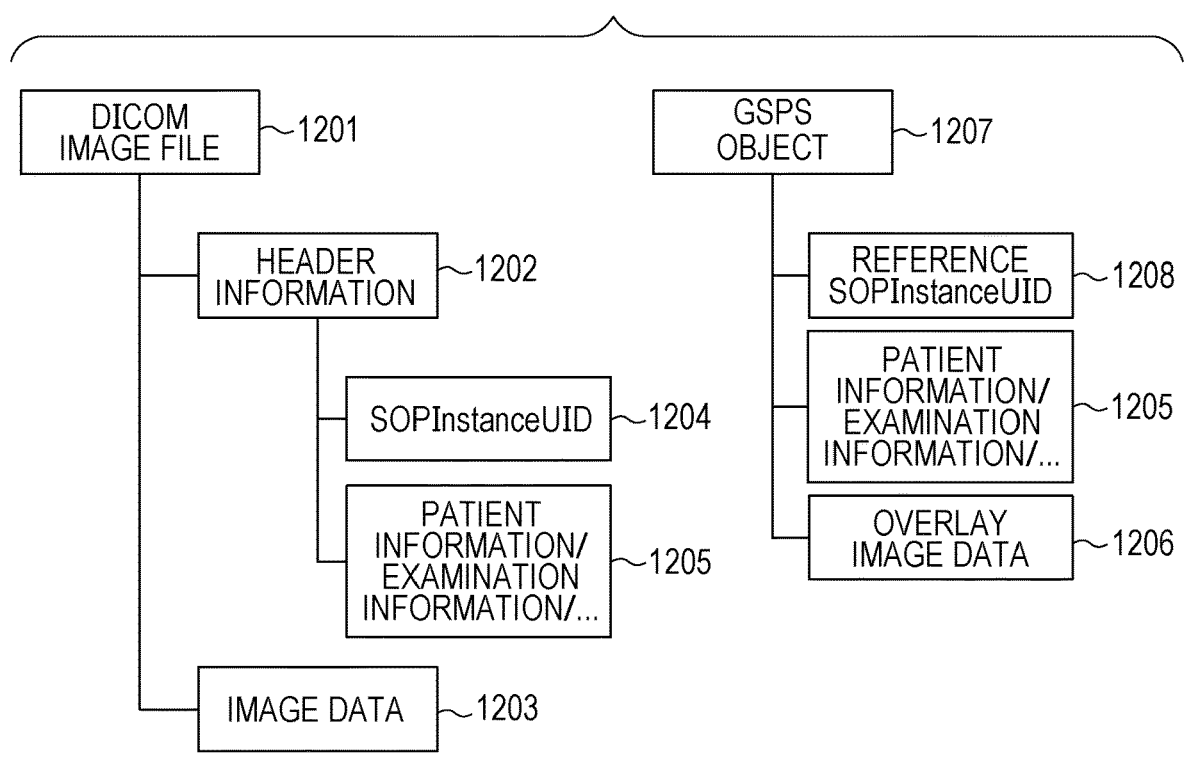
FIG. 12B is a diagram illustrating an example of information generated by the control device according to the embodiment of the present invention.

FIGS. 12A and 12B are diagrams illustrating an example of the structure of generating an object to be transmitted to an external device following the DICOM standard. An object to be generated following the DICOM standard includes information of at least one of examination instance ID, series UID, patient ID, examination UID, and information of date and time relating to examination. The information of date and time relating to examination includes information of at least one of examination date, examination time, time of acquisition of ultrasound image, and time of acquisition of photoacoustic image. The time of acquisition of ultrasound image is, for example, the time at which acquisition of all ultrasound wave signals has been completed to generate one B-mode image. The time of acquisition of photoacoustic image is, for example, the time at which photoacoustic signals used for generating this photoacoustic image were obtained. The object in the present embodiment is transmitted by two types of methods set by the settings 1308 in a superimposed image settings screen 1301 exemplarily illustrated in FIG. 13.

FIG. 12A is a diagram illustrating an example of the configuration where "transmit as supplementary information of base image" or "transmit as individual image object" is selected in the settings 1308. A DICOM image file 1201 that is an object to be transmitted to an external device includes header information 1202 and image data 1203. The header information 1202 includes at least a SOP Instance UID 1204 that uniquely identifies the DICOM image file 1201, text string data 1205 of patient information, examination information, and so forth, and overlay image data 1206. The overlay image data 1206 is image data of a layer image superimposed on the image data 1203. In a case where the settings 1308 are set to "transmit as supplementary information of base image", multiple overlay image data 1206 may be registered to one DICOM image file 1201. In a case where the settings 1308 are set to "transmit as individual image object", the overlay image data 1206 is not generated. The DICOM image file 1201 exemplified in FIG. 12A corresponds to the individual image information 1103 in FIG. 11, for example. Note that a composite image is generated as a single DICOM image file 1201. The DICOM image file 1201 including the composite image corresponds to the composite image information 1104 illustrated in FIG. 11, for example.

FIG. 12B is a diagram illustrating an example of the configuration in a case where "transmit as reference object of base image" is set for the settings 1308. The DICOM image file 1201 includes the header information 1202 and the image data 1203. The header information 1202 includes SOP Instance UID 1204, and text string data 1205 of patient information, examination information, and so forth. The header information 1202 does not include overlay image data 1206. Overlay image data corresponding to the layer image superimposed on the image data 1203 is generated individually as a GSPS object 1207, for example. The GSPS object 1207 includes the base image on which the overlay image data 1206 is to be overlaid, and the reference SOP Instance UID 1208 to identify the corresponding DICOM image file 1201. The GSPS object 1207 includes text string data 12056 such as patient information, examination information, and so forth, and overlay image data 1206. The layer image data and GSPS object 1207 are generated in a one on one manner. Multiple GSPS objects 1207 can set one DICOM image file 1201 to the reference SOP Instance UID 1208. The GSPS object 1207 exemplified in FIG. 12B corresponds to the superimposing reference image information 1105 illustrated in FIG. 11, for example. According to this configuration, the control device 101 can transmit objects for superimposed display at external devices.

FIG. 13 is a diagram illustrating an example of a screen to perform settings regarding superimposed display. The superimposed image settings screen 1301 in FIG. 13 performs settings relating to superimposed display for each imaging procedure. The superimposed image settings screen 1301 includes imaging procedure name 1302, settings 1303 through 1310, a cancel portion 1312, and an OK portion 1313.

The imaging procedure name 1302 is a region for displaying the name of the imaging procedure as a settable increment in the superimposed image settings screen 1301. In the settings 1303, whether to apply settings to all image data acquired in the imaging system 100 or not, i.e., whether or not to perform batch settings, is selected. If not batch settings, superimposed display is performed based on settings set for each imaging procedure.

Although an example of performing settings related to superimposed display for each imaging procedure is illustrated in FIG. 13, this is not restrictive, and settings may be made in any other increment. For example, settings relating to superimposed display may be applied to all image data acquired in the imaging system 100 by batch settings. For example, in the case of batch settings, the imaging procedure name 1302 and settings 1303 are hidden from display, and the superimposed image settings screen 1301 is displayed with the display region moved up.

A method for selecting image data to be included in the superimposed display for output, to an external device, of an object displayable as a superimposed image is selected at the settings 1304. Selection is made in the settings 1304 from "default selecting method", "customized selecting method", "select based on superimposed display history", and "select based on post-processing history".

Customization settings relating to superimposed display are performed at the settings 1305. In FIG. 13, the settings 1305 is a button for instructing displaying of a customization settings screen 1401. Customization settings will be described later with reference to FIG. 14.

The method of superimposing image data other than the image data selected as the base image, on this base image, is selected at the settings 1306. Selection is made from, for example, "superimpose individually", "composite layer images", and "composite base image and layer image" at the settings 1306.

The display method of the superimposed display is selected at the settings 1307. Selection is made from, for example, "transmissive display", "display overlaid portions using different color", "superimposed display according to order", "masked display" and "difference display" at the settings 1307. Examples of superimposed display performed by the respective display methods are illustrated in FIGS. 8A through 8H. Note that the settings 1307 are also used when generating composite images as well.

The method of transmitting an object for superimposed display is selected at the settings 1308. Selection is made from, for example, "transmit as supplementary information of base image", "transmit as reference object of base image", and "transmit as individual image object" at the settings 1308.

At the settings 1309, whether or not to display the warning dialog 1001 in a case where there is image data that is not used for a base image or layer image for superimposed display, not used in a composite image, and not individually transmitted either, at the time of instructing external transmission, is selected. In a case where the settings 1309 are ON, the warning dialog 1001 is displayed in a case where there is image data not transmitted to an external device. In a case where the settings 1309 are OFF, the warning dialog 1001 is not displayed even if there is image data that is not transmitted to an external device.

Whether or not to individually transmit image data used in a superimposed image or composite image is selected at the settings 1310. In a case where the settings 1310 are ON, an individual image object including image data regarding which the external transmission permission/non-permission information 307 is set to ON is transmitted to an external device, regardless whether or not this image data is used as a base image or layer image for superimposed display or in a composite image. In a case where the settings 1310 are OFF, the individual image object including image data used as a base image or layer image for superimposed display or in a composite image is not transmitted to an external device regardless of the external transmission permission/non-permission information 307. Accordingly, the amount of data transmitted to external devices can be reduced.

The cancel portion 1312 is a button for instructing discarding of the contents set in the superimposed image settings screen 1301. Pressing the cancel portion 1312 closes the superimposed image settings screen 1301.

The OK portion 1313 is a button for instructing finalization of the contents set in the superimposed image settings screen 1301. Pressing the OK portion 1313 saves the contents that have been set in the settings saving unit 124, and the superimposed image settings screen 1301 is closed.

FIG. 14A is a diagram illustrating an example of a customization settings screen 1401. The customization settings screen 1401 is a screen for performing customization settings relating to superimposed display. The customization settings screen 1401 includes a list display switching portion 1402, an adding portion 1403, an editing portion 1404, a imaging procedure name 1405, a list display portion 1406, a cancel portion 1407, and an OK portion 1408.

The list display switching portion 1402 is a region for instructing switching of contents displayed as a list in the list display portion 1406. In the example illustrated in FIG. 14A, selection of the content to be displayed as a list is made from "superimposed image" and "composite image". In a case where the display content does not all fit in the list display portion 1406, buttons for switching the content displayed in the list display portion 1406 are displayed in the list display switching portion 1402.

The adding portion 1403 is a button for instruction of adding new customization settings. When the adding portion 1403 is pressed, a popup display is made of an individual settings dialog 1409 exemplarily illustrated in FIG. 14B on the customization settings screen 1401. The user can add customization settings by inputting into the individual settings dialog 1409.

The editing portion 1404 is a button for instructing editing of the customization settings selected at the list display portion 1406. When the editing portion 1404 is pressed, a popup display is made of the individual settings dialog 1409 on the customization settings screen 1401. The user can edit selected customization settings by inputting into the individual settings dialog 1409.

The imaging procedure name 1405 is a region for displaying the name of the imaging procedure as a settable increment in the customization settings screen 1401.

The list display portion 1406 is a region displaying the contents of customization settings relating to superimposed display in a list. In a case where "superimposed image" is selected as the contents to display in the customization settings screen 1401, information indicating a base image, and layer images to be superimposed on the base image, are displayed in the list display portion 1406. Information relating to one image data is displayed in one cell in the list display portion 1406. The type of image of the image data, and superimposing method as to the base image, are displayed in individual cells. In a case where one layer image is a composite image obtained by compositing multiple image data, the image types of all image data used in this composite image are displayed in the cell. In a case where "composite image" is selected as the content to display in the customization settings screen 1401, image data to use as the base image when compositing, and layer images to be superimposed on this base image and composited, are displayed in the list display portion 1406. The image types of the image data of the layer images, and the compositing method as to the base image, is displayed. Although an example where information indicating the image type and superimposing method is displayed as text strings in the cells in the list display portion 1406 is illustrated in FIG. 14A, other forms such as thumbnail images or the like may be displayed, as long as a form that the user can understand this information.

The cancel portion 1407 is a button for instructing discarding of the editing contents of the customization settings. When the cancel portion 1407 is pressed, the contents of the edited customization settings are discarded, and the customization settings screen 1401 is closed.

The OK portion 1408 is a button for instructing finalization of the editing contents of the customization settings. When the OK portion 1408 is pressed, the contents of the edited customization settings are finalized, and information of these settings is saved in the settings saving unit 124. The customization settings screen 1401 is then closed.

FIG. 14B is an example of the individual settings dialog 1409 for individually performing customization settings relating to superimposed display. The customization settings screen 1401 includes a imaging procedure name 1410, settings 1411 through 1413, a cancel portion 1414, and an OK portion 1415.

The imaging procedure name 1410 is a region for displaying the name of the imaging procedure as a settable increment in the customization settings screen 1401.

The image type of the image data used for the base image is selected at the settings 1411. The image type of the image data to be displayed superimposed on the base image, or of image data to be composited, i.e., layer image, is selected at the settings 1412. Images of image types other than the image type of the base image can each be selected as layer images, and the order of superimposing can be set at the settings 1412. A superimposing method selecting portion 1413 is the same as the settings 1307 exemplarily illustrated in FIG. 13, so the above description will be incorporated here by reference, and detailed description will be omitted.

The cancel portion 1414 is a button for instructing discarding of the editing contents of the individual settings. When the cancel portion 1414 is pressed, the contents of the edited individual settings are discarded, and the individual settings dialog 1409 is closed. The OK portion 1415 is a button for instructing finalization of the editing contents of the individual settings. When the OK portion 1415 is pressed, the contents of the edited individual settings are finalized, the individual settings dialog 1409 is closed. The display contents of the list display portion 1406 in the customization settings screen 1401 are edited by way of the individual settings dialog 1409, and finalized contents are updated.

Thus, the plurality of image data obtained by the imaging system 100 is output as objects suitable for superimposed display at the PACS 113 or viewer 114, for example. An example of acquiring ultrasound wave signals and photoacoustic signals by the imaging system 100 and outputting image data generated from the acquired signals to the external device will be described.

The signal acquisition unit 123 acquires ultrasound wave signals and photoacoustic signals under control of the imaging control unit 122 and examination control unit 125, based on information obtained from the ordering system 112 or information set by the user. For example, the probe 102 is brought into contact with the subject body by the user, the subject body is irradiated by ultrasound waves, reflected echoes are received, and a series of ultrasound wave signals is obtained. A series of ultrasound images is displayed on the display unit 104 by the image processing unit 121 and input/output control unit 126.

The user performs input of operations as appropriate to irradiate the subject body by light from the probe 102 at a desired timing, receives acoustic waves, and obtains photoacoustic signals. An absorption coefficient image that is an example of a photoacoustic image is displayed on the display unit 104 superimposed on the ultrasound image, by the image processing unit 121 and input/output control unit 126.

Irradiation of the subject body by ultrasound waves and light ends, and the control device 101 starts processing for selecting the output form of the acquired image data (FIG. 4). The examination control unit 125 acquires shot image information 302 (FIG. 3) relating to the series of ultrasound images, and the photoacoustic image acquired in conjunction at a desired timing (step S402). The examination control unit 125 then identifies the photoacoustic image acquired at the desired timing, and ultrasound images acquired at a time near this timing, as a correlated series of images, and acquires shot image information 302 thereof (step S403), for example.

Combinations of image data for generating objects for superimposed display are identified based on settings exemplarily illustrated in FIG. 13 (steps S404 through S408). The image data to be used for superimposed display is selected, and the superimposing method is decided (FIG. 5). The external transmission information generating unit 127 selects, for example, a B-mode image that is an example of an ultrasound image as the base image, and an oxygen saturation image that is an example of a photoacoustic image as a layer image, based on the settings exemplarily illustrated in FIGS. 13 through 14B (steps S502 through S503). These selections are performed based on customization settings made by the user, for example. A desired form is selected from various superimposed display forms such as illustrated in FIGS. 8A through 8H, based on user settings. A composite image is then generated (steps S506 through S510), or data for superimposed display is generated (step S510).

An object for superimposed display is transmitted to an external device such as the PACS 113 in accordance with the instruction for output. Determination is made regarding whether the image data instructed to be transmitted to the external device is a failed shot or not (Step S604), and further determination is made regarding whether or not to transmit to the external device (steps S607 through S610 and S613). An object for outputting to the external device is generated based on the settings exemplarily illustrated in FIGS. 13 through 14B (step S616), and transmitted (step S617). Image data that is not a failed shot and is suitable for observation, for example, is transmitted to the external device by the processing illustrated in FIG. 6. Assuming that the transmission method of image data to the external device has been set to "transmit as supplementary information of base image" in the settings 1308 for example, a DICOM image file 1201 having the ultrasound image (B-mode image) that is the base image is generated (FIG. 12). The photoacoustic image (oxygen saturation image) that is a layer image is included in the overlay image data 1206 included in this DICOM image file 1201. In another example, assuming that the transmission method of image data to the external device has been set to "transmit as reference object of base image" in the settings 1308, a DICOM image file 1201 having the ultrasound image (B-mode image) that is the base image is generated (FIG. 12). Superimposing reference image information 1105 (FIG. 11) corresponding to the oxygen saturation image is then generated. In a case where a color display of the oxygen saturation image is desired, the superimposing reference image information 1105 is a CSPS object (omitted from illustration), for example. The CSPS object (omitted from illustration) has the same configuration as the GSPS object 1207 illustrated in FIG. 12. The CSPS object (omitted from illustration) has a SOP Instance UID corresponding to the base image for superimposing the oxygen saturation image as a layer image, i.e., the DICOM image file 1201 for the B-mode image. Accordingly, superimposed display with the B-mode image as the base image can be realized at the viewer 114 based on the oxygen saturation image CSPS object (omitted from illustration). The user can easily perform superimposed display of a suitable form.

Modifications

Although an example of generating an object of display at an external device, in a form of suitable superimposed display of a plurality of image data acquired at the imaging system 100 in the above embodiments, the present invention is not restricted to this arrangement. For example, the above-described processing may be realized as a report system. A report system is a system where the results of interpreting, where a physician observes image data of the subject and makes a diagnosis on the pathological condition and so forth of the subject based on the features instructed in the image data, are generated as an interpretation report. Superimposed images, composite images, and data for superimposed display, generated at the imaging system 100, are set as key images in an interpretation report by the above-described processing, for example, thereby supporting the physician in generating an interpretation report.

An example has been described in the above embodiment, where an object for displaying in a suitable superimposed display form at an external device when outputting a plurality of image data obtained at the imaging system 100 to the external device, but the present invention is not restricted to this arrangement. For example, an object for superimposed display at the external device may be newly generated based on an object for output to the external device that has already been generated. For example, the control device 101 references a DICOM image file of a B-mode image already generated, and the user inputs operations relating to superimposed display. The external transmission information generating unit 127 identifies the image data for superimposed display with this B-mode image, based on supplemental information included in the DICOM image file. For example, the examination in which the B-mode image was taken is identified using at least one of the examination instance ID, series UID, patient ID, examination UID, and information of date and time relating to examination, included in the DICOM image file. The information of date and time relating to examination includes information of at least one of examination date, examination time, time of acquisition of ultrasound image, and time of acquisition of photoacoustic image. The external transmission information generating unit 127 selects image data for superimposed display with this B-mode image from the series of image data acquired by the specified examination. The examination control unit 125 registers information relating to this superimposed display in the superimposed display history information 310 or post-processing history information 311 of the shot image information 302 relating to this B-mode image. In a case where an instruction to transmit the data relating to this superimposed display to the external device is made by the user, the external transmission information generating unit 127 generates the object for this superimposed display based on the above-described processing.

In the above embodiment, an example has been described where image information to serve as a reference is selected in step S404, and thereafter a base image and layer image are selected in step S409 and a superimposed image is displayed, as described with reference to FIG. 4, but the present invention is not restricted to this arrangement. For example, the selection of image information to serve as a reference shown in step S404 does not have to be performed. In this case, a combination not included in superimposed image identification information is selected from the correlated series of image information obtained in step S403, and the flow advances to step S409.

In the above embodiment, an example has been described where information to identify the superimposing order, base image, and layer image is used as information for superimposed display, but this present invention is not restricted to this. Processing for positioning a plurality of image data may further be performed, and information indicating positional displacement among image data, and information indicating offset, may be used as information for superimposed display.

The present invention can also be realized by supplying a program that realizes one or more functions of the above-described embodiment to a system or device via a network or storage medium, and one or more processors of a computer in the system or device reading out and executing the program. The present invention can also be realized by a circuit (e.g., an application-specific integrated circuit (ASIC)) that realizes one or more functions.

The control device in the above-described embodiment may be realized as a standalone device, or may be realized in an arrangement where multiple devices are communicably combined with each other and execute the above-described processing, and both arrangements are included in an embodiment of the present invention. The above-described processing may be executed by a shared server device or server group. It is sufficient for the control device and multiple devices making up the control system to be communicable at a predetermined communication rate, and do not need to be in the same facility or within the same nation.

An embodiment of the present invention includes a form of a software program that realizes the functions of the embodiment described above to a system or device, and a computer of the system or device reading out and executing code of the program that has been supplied thereto.

Accordingly, the program code that is installed to a computer to realize processing according to the embodiment by the computer is in itself an embodiment of the present invention. Also, the functions of the embodiment described above can be realized by the processing where an operating system (OS) or the like performing part of all of the actual processing, in the computer based on instructions included in the program that the computer has read out.

Forms obtained by appropriately combining the above-described embodiments are also included in an embodiment of the present invention.

The present invention is not restricted to the above-described embodiments, and various changes and modifications can be made without departing from the spirit and scope of the present invention. Accordingly, the following Claims are attached to publicly set forth the scope of the present invention.

The control device according to an embodiment of the present invention can display a desired image on a viewer.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. A control device comprising:
a memory storing a program; and
one or more processors which, by executing the program, cause the control device to:
acquire an ultrasound image and plural kinds of photoacoustic images taken in an examination, wherein the plural kinds of photoacoustic images are generated based on photoacoustic waves occurring in an irradiation of a subject body by light;
generate an image list corresponding to the plural kinds of photoacoustic images including at least two images of an initial acoustic pressure distribution image, a light fluence distribution image, an absorption coefficient distribution image, and an oxygen saturation distribution image;
select, from the ultrasound image and the plural kinds of photoacoustic images, a first image; and a second image to be displayed superimposed on the first image, wherein the ultrasound image is selected as the first image and the second image is selected from the plural kinds of the photoacoustic images, by an operating unit for transmitting information relating to input of user operations to the control device using the image list indicating names of the plural kinds of photoacoustic images;
and
display, on a display unit, the image list indicating names of the plural kinds of photoacoustic images, selection information corresponding to the second image selected from the plural kinds of the photoacoustic images, and a superimposed image in which the second image is superimposed on the first image.

2. The control device according to claim 1, wherein a third image for superimposed display on the first image and second image is selected, from the plural kinds of photoacoustic images.

3. The control device according to claim 2, wherein an object is generated where an order of superimposing the second image and the third image on the first image is identifiable.

4. The control device according to claim 1, wherein supplementary information is attached to the ultrasound image and the plural kinds of photoacoustic images, and the supplementary information includes information of time at which the ultrasound wave signals and photoacoustic signals each were acquired in the examination, as examination information relating to an examination order.

5. The control device according to claim 4, wherein the supplementary information includes information of at least one of examination instance ID, series UID, patient ID, examination UID, and information of date and time relating to examination.

6. The control device according to claim 5, wherein the information of date and time relating to the examination includes at least one of examination date, examination time, time of acquisition of the ultrasound image, and time of acquisition of the photoacoustic image.

7. The control device according to claim 1, further caused to generate the second image as overlay image data as to the first image, and generates a DICOM image file including the first image and the overlay image data as the object, as information for superimposed display of the second image on the first image.

8. The control device according to claim 1, further caused to generate a DICOM image file including the first image, and generate information for superimposed display of the second image on the first image.

9. The control device according to claim 1, wherein the information for displaying the second image superimposed on the first image includes at least information for identifying the first image.

10. The control device according to claim 9, wherein the information for displaying the second image superimposed on the first image includes information indicating an order of superimposing the second image, out of the plural kinds of images to be superimposed on the first image, on the first image.

11. A control method comprising:
acquiring an ultrasound image and plural kinds of photoacoustic images taken in an examination, wherein the plural kinds of photoacoustic images are generated based on photoacoustic waves occurring in an radiation of a subject body by light;
generating an image list corresponding to the plural kinds of photoacoustic images including at least two images of an initial acoustic pressure distribution image, a light fluence distribution image, an absorption coefficient distribution image, and an oxygen saturation distribution image;
selecting, from the ultrasound image and the plural kinds of photoacoustic images, a first image, and a second image to be displayed superimposed on the first image, wherein ultrasound image is selected as the first image and the second image is selected from the plural kinds of photoacoustic images, by an operating unit for transmitting information relating to input of user operations to the control device using the image list indicating names of the plural kinds of photoacoustic images; and
displaying, on a display unit, the image list indicating names of the plural kinds of photoacoustic images, selection information corresponding to the second image selected from the plural kinds of the photoacoustic images, and a superimposed image in which the second image is superimposed on the first image.

12. A non-transitory recording medium storing a program that causes a computer to execute acquiring an ultrasound image and plural kinds of photoacoustic images taken in an examination, wherein the plural kinds of photoacoustic images are generated based on photoacoustic waves occurring in an irradiation of a subject body by light;
generating an image list corresponding to the plural kinds of photoacoustic images including at least two images of an initial acoustic pressure distribution image, a light fluence distribution image, an absorption coefficient distribution image, and an oxygen saturation distribution image;
selecting, from the ultrasound image and plural kinds of photoacoustic of images, a first image and a second image to be displayed superimposed on the first image, wherein the ultrasound image is selected as the first image and the second image is selected from the plural kinds of the photoacoustic images, by an operating unit for transmitting information relating to input of user operations to the control device using the image list indicating names of the plural kinds of photoacoustic images; and
displaying, on a display unit, the image list indicating names of the plural kinds of photoacoustic images, selection information corresponding to the second image selected from the plural kinds of the photoacoustic images, and a superimposed image in which the second image is superimposed on the first image.

13. The control device according to claim 1, wherein the image list includes a superposition instruction icon for instructing superposition display of each of the plural kinds of photoacoustic images.

14. The control device according to claim 1, wherein, in the case where the superposition instruction icon is set to ON, the photoacoustic image corresponding to the superposition instruction icon set to ON is superposed as the second image.

15. The control device according to claim 1, wherein, in the case where the superposition instruction icon is set to OFF, the photoacoustic image corresponding to the superposition instruction icon set to OFF is not superposed as the second image.

16. The control device according to claim 1, wherein, the superimposing instruction icon is set to OFF for the photoacoustic image regarding which superimposed display is not possible in the plural kinds of photoacoustic images.

* * * * *